United States Patent
Li et al.

(10) Patent No.: US 11,091,511 B2
(45) Date of Patent: Aug. 17, 2021

(54) PANAXDIOL-TYPE GINSENOSIDE DERIVATIVE, PREPARATION METHOD THEREFOR AND USE THEREOF

(71) Applicants: ARMY MEDICAL UNIVERSITY, Chongqing (CN); CHONGQING PUDI BIO-PHARMACEUTICAL CO. LTD, Chongqing (CN)

(72) Inventors: Xiaohui Li, Chongqing (CN); Yi Jia, Chongqing (CN); Yan Huang, Chongqing (CN)

(73) Assignees: ARMY MEDICAL UNIVERSITY, Chongqing (CN); CHONGQING PUDI BIO-PHARMACEUTICAL CO. LTD, Chongqing (CN)

( * ) Notice: Subject to any disclaimer, the term of this patent is extended or adjusted under 35 U.S.C. 154(b) by 0 days.

(21) Appl. No.: 16/333,803

(22) PCT Filed: Sep. 15, 2017

(86) PCT No.: PCT/CN2017/101880
§ 371 (c)(1),
(2) Date: Mar. 15, 2019

(87) PCT Pub. No.: WO2018/050099
PCT Pub. Date: Mar. 22, 2018

(65) Prior Publication Data
US 2019/0256549 A1    Aug. 22, 2019

(30) Foreign Application Priority Data

Sep. 19, 2016    (CN) .......................... 201610828140.7

(51) Int. Cl.
| | |
|---|---|
| *C07J 43/00* | (2006.01) |
| *A61P 9/10* | (2006.01) |
| *C07H 15/18* | (2006.01) |
| *C07J 17/00* | (2006.01) |
| *C07J 41/00* | (2006.01) |
| *C07H 1/00* | (2006.01) |

(52) U.S. Cl.
CPC .............. *C07J 43/003* (2013.01); *A61P 9/10* (2018.01); *C07H 1/00* (2013.01); *C07H 15/18* (2013.01); *C07J 17/00* (2013.01); *C07J 41/0033* (2013.01); *C07J 41/0055* (2013.01)

(58) Field of Classification Search
CPC ...... C07J 43/003; C07J 41/0055; C07H 15/18
See application file for complete search history.

(56) References Cited

U.S. PATENT DOCUMENTS

2011/0212909 A1    9/2011    Wen et al.

FOREIGN PATENT DOCUMENTS

| CN | 101284858 A | 10/2008 |
|---|---|---|
| CN | 101580530 A  * | 11/2009 |
| CN | 101653447 A | 2/2010 |
| CN | 102766187 A | 11/2012 |
| CN | 103505462 A | 1/2014 |
| CN | 104586860 A | 5/2015 |
| CN | 106632570 A | 5/2017 |
| KR | 20090115280 A | 11/2009 |
| WO | 2004058796 A1 | 7/2004 |
| WO | 2013189229 A1 | 12/2013 |

OTHER PUBLICATIONS

Liu, J. et al., European Journal of Medicinal Chemistry, "Discovery, synthesis, and structure-activity relationships of 20(S)-protopanaxadiol (PPD) derivatives as a novel class of AMPKalpha2beta1gamma1 activators" (Year: 2014).*
Cao, F. et al., Molecular Pharmaceutics, 2012, vol. 9, 2127-2135 (Year: 2012).*
CN 101580530A, published 2009; English machine translation, obtained from epo.org on Feb. 14, 2020; 16 total pages (Year: 2009).*
International Search Report for International Application No. PCT/CN2017/101880, dated Dec. 20, 2017, 2 pages.
English translation of Office Action for RU Application No. 2019107605/04(014772), dated Oct. 21, 2019, 16 pages.
Liu, Ya-Fei et al., "25-Methoxylprotopanaxadiol derivatives and their anti-proliferative activities," Steroids vol. 78 (2013), pp. 1305-1311.
India Examination Report for IN Application No. 201917011587 dated May 28, 2020; 6 pp.

* cited by examiner

*Primary Examiner* — Bahar Craigo
(74) *Attorney, Agent, or Firm* — Armstrong Teasdale LLP

(57) ABSTRACT

Provided are panaxdiol-type ginsenoside derivatives having structures as shown in formula I or formula II. Also provided are the uses thereof in the preparation of drugs for preventing and treating atherosclerosis. The panaxdiol-type ginsenoside derivatives have low cytotoxicities, can significantly reduce the percentages of the areas of atherosclerotic plaques in apoE−/− mice, can also effectively reduce the levels of low-density lipoprotein cholesterol and increase the levels of high-density lipoprotein cholesterol in serums of mice, and can significantly reduce the local TNF-α levels in the arteries of apoE−/− mice and have good anti-inflammatory effects; at a dose of 30 μM, the panaxdiol-type ginsenoside derivatives can significantly reduce the degrees of the formation of RAW264.7 cell-derived foam cells. In addition, the preparation methods for the panaxdiol-type ginsenoside derivatives are easy to operate and obtain high yields.

10 Claims, No Drawings

PANAXDIOL-TYPE GINSENOSIDE DERIVATIVE, PREPARATION METHOD THEREFOR AND USE THEREOF

CROSS-REFERENCE TO RELATED APPLICATIONS

This application is a U.S. National Phase Application of PCT/CN2017/101880, filed Sep. 15, 2017, which claims the benefit of priority to CN Application No. 201610828140.7, filed Sep. 19, 2016, the contents of which are hereby expressly incorporated by reference in their entirety.

TECHNICAL FIELD

The present invention belongs to the technical field of medicine, and particularly relates to panaxdiol-type ginsenoside derivatives, preparation methods and uses thereof.

TECHNICAL BACKGROUND

Atherosclerosis is one of the diseases with high incidence nowadays. It is the common pathological basis of many serious cardiovascular diseases (such as coronary heart disease, angina pectoris, cerebrovascular embolism, etc.), posing a serious threat to human health. At present, drugs for treating atherosclerosis mainly regulate blood lipids, comprising statins, fibrates and niacins. Although the above categories of drugs can achieve good effects of lowering blood lipid, the incidence of atherosclerosis remains high and increases year by year, indicating that drugs only have the function of regulating blood lipid cannot meet the requirements of preventing and treating atherosclerosis. Studies have shown that inflammatory immune factors play important roles in the pathogenesis of atherosclerosis, and atherosclerosis has been recognized as a chronic inflammatory disease of blood vessels. Therefore, it is important to develop anti-atherosclerotic drugs that have effects of regulating blood lipids and anti-inflammatory activities simultaneously.

Since ancient times, *ginseng* has been hailed as the "King of Herbs", which has the effects of replenishing vital energy, restoring the pulse and preventing collapse, invigorating the spleen and tonifying the lungs, promoting the secretion of saliva or body fluid and replenishing blood, tranquilizing the mind and promoting the intelligence. Ginsenoside is the main active ingredient of *ginseng* and has the main pharmacological activity of *ginseng*. There are about more than 40 kinds of ginsenoside monomers with identified structures. Studies have found that panaxdiol-type ginsenosides have certain effects of preventing and treating atherosclerosis, and further mechanism studies have shown that their pharmacological effects comprise regulating blood lipids, reducing inflammation and reducing smooth muscle proliferation etc., but their activities are low, and they have certain cytotoxicities and lack practical application value.

SUMMARY OF THE INVENTION

The object of the present invention is to provide panaxdiol-type ginsenoside derivatives, preparation methods and uses thereof, and it is intended to provide panaxdiol-type ginsenoside derivatives having relatively high activities and low toxicities that can be used in the preparation of medicaments for preventing and treating atherosclerosis.

The present invention provides a panaxdiol-type ginsenoside derivative, having the structure shown in formula I or formula II:

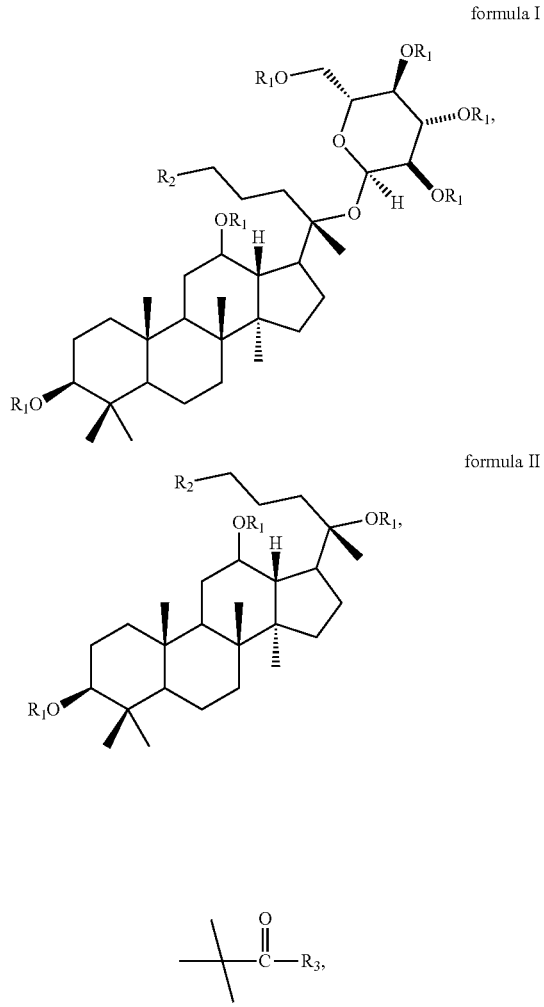

in formula I and formula II, $R_1$ wherein, $R_3$ is a C1-C4 alkyl;

$R_2$ has the structure shown in formula III:

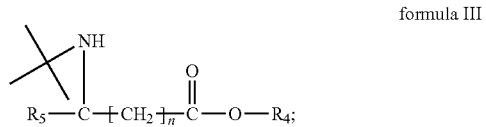

in formula III, n=0, 1 or 2, $R_4$ is methyl or ethyl, $R_5$ is one of a hydrogen atom, a substituted or unsubstituted C1-C5 alkyl, a substituted or unsubstituted benzyl and a C4-C9 heterocycloalkyl.

Preferably, $R_5$ is a C1-C5 alkyl, a C1-C5 hydroxyalkyl or a C3-C5 ester alkyl.

Preferably, $R_5$ is —$CH_2CH(CH_3)_2$, —$CH(CH_3)_2$, —$CH(OH)CH_3$, —$CH_2OH$, —$CH_2CH_2COOCH_2CH_3$ or —$CH_2COOCH_2CH_3$.

Preferably, R₅ is

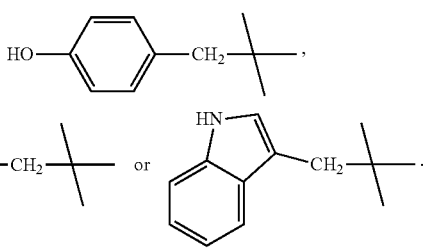

Preferably, R₂ is

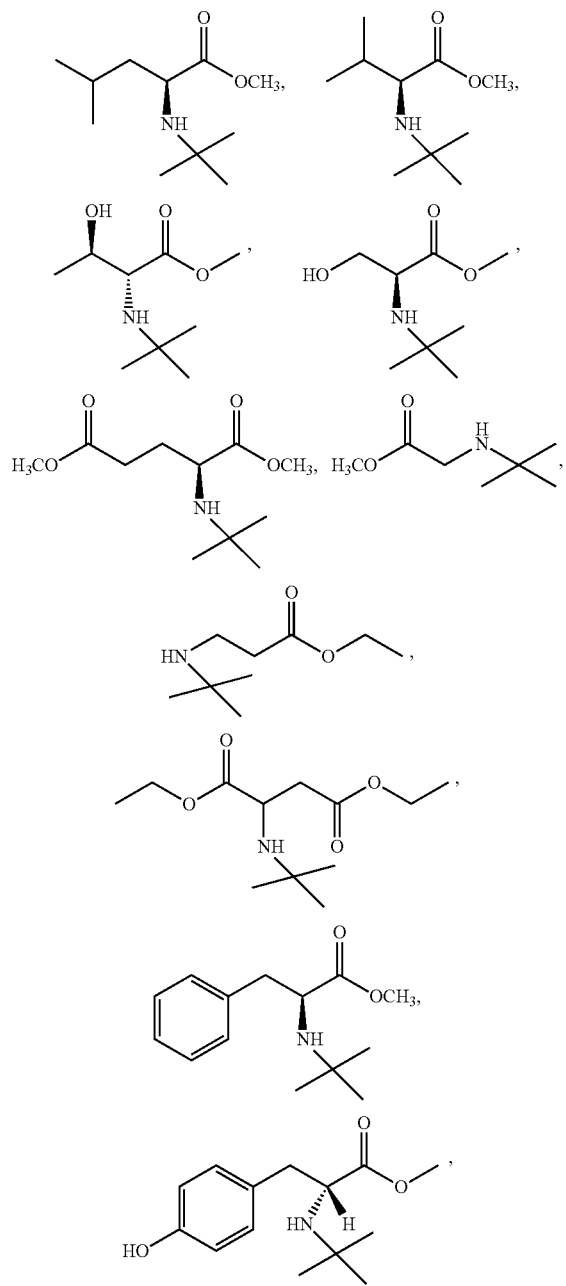

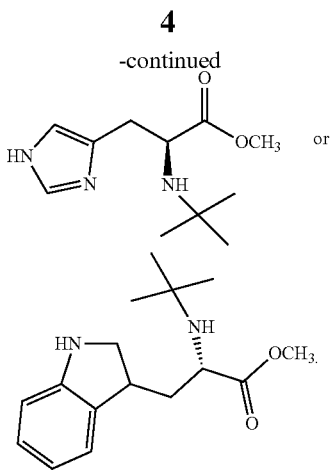

Preferably, R₁ is

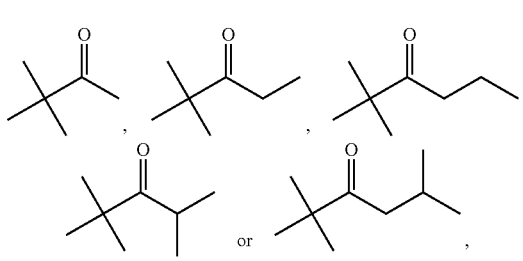

The present invention provides a preparation method of the panaxdiol-type ginsenoside derivative described in the above technical solution, comprising the following steps:

(1) subjecting a parent compound to a nucleophilic substitution reaction with an acid anhydride in the presence of an alkaline reagent to obtain a first intermediate product;

(2) subjecting the first intermediate product in step (1) to an oxidation reaction in the presence of an oxidizing agent and an organic solvent to obtain a second intermediate product;

(3) subjecting the second intermediate product in step (2) to a reductive amination reaction with an amino compound in the presence of an organic solvent and a reducing agent to obtain a panaxdiol-type ginsenoside derivative having the structure shown in formula I or formula II;

wherein the parent compound in step (1) has the structure shown in formula IV or formula V:

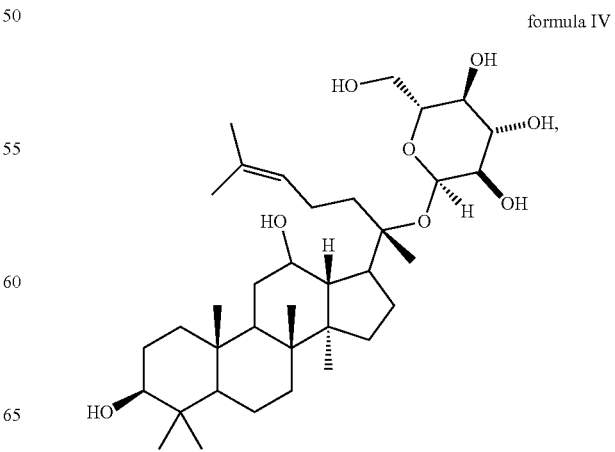

formula IV

-continued formula V

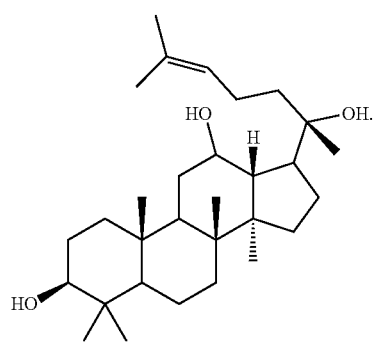

formula I

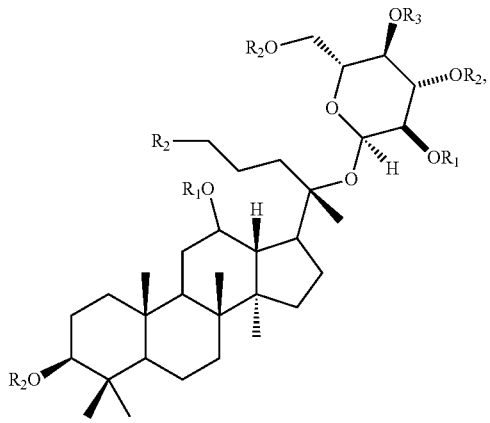

formula II

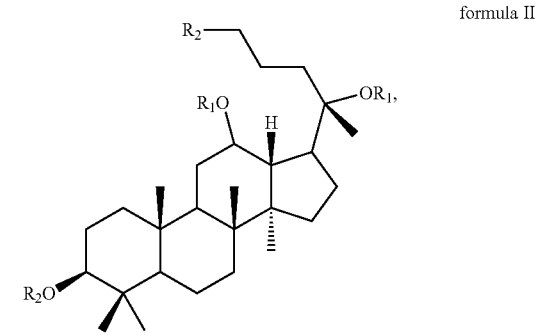

Preferably, the oxidation reaction in step (2) is specifically:

(21) subjecting the first intermediate product in step (1) to a primary oxidation reaction in the presence of a first oxidizing agent and an organic solvent to obtain a precursor of the second intermediate product;

(22) subjecting the precursor of the second intermediate product in step (21) to a secondary oxidation reaction in the presence of a second oxidizing agent and an organic solvent to obtain the second intermediate product.

Preferably, the first oxidizing agent in step (21) is hydrogen peroxide, hypochlorous acid, calcium hypochlorite, acetone peroxide or meta-chloroperbenzoic acid; the second oxidizing agent in step (22) is potassium permanganate, manganese dioxide, periodic acid or Sarrett reagent.

The present invention provides the use of the panaxdiol-type ginsenoside derivative described in the above technical solution or the panaxdiol-type ginsenoside derivative obtained from the preparation method described in the above technical solution in the preparation of a medicament for preventing and treating atherosclerosis.

The present invention provides panaxdiol-type ginsenoside derivatives having the structure shown in formula I or formula II, and the panaxdiol-type ginsenoside derivatives provided by the present invention have low cytotoxicities, can significantly reduce the percentages of the areas of atherosclerotic plaques in apoE−/− mice, can also effectively reduce the levels of low-density lipoprotein cholesterol and increase the levels of high-density lipoprotein cholesterol in the serums of mice, and can significantly reduce the local TNF-α levels in the arteries of apoE−/− mice and have good anti-inflammatory effects; at a dose of 30 μmol/L, the panaxdiol-type ginsenoside derivatives can significantly reduce the degrees of the formation of RAW264.7 cell-derived foam cells, which means that the panaxdiol-type ginsenoside derivatives provided in the present invention can be used as active ingredients for preparing medicaments for preventing and treating atherosclerosis.

In addition, the present invention provides preparation methods for the panaxdiol-type ginsenoside derivatives, which are easy to operate and obtain high yields.

EMBODIMENTS

The present invention provides a panaxdiol-type ginsenoside derivative, having the structure shown in formula I or formula II:

in formula I and formula II, $R_1$ is

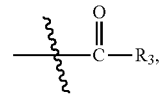

wherein, $R_3$ is a C1-C4 alkyl;

$R_2$ has the structure shown in formula III:

formula III

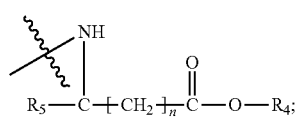

in formula III, n=0, 1 or 2, $R_4$ is methyl or ethyl, $R_5$ is one of a hydrogen atom, a substituted or unsubstituted C1-C5 alkyl, a substituted or unsubstituted benzyl and a C4-C9 heterocycloalkyl.

In the present invention, $R_1$ is

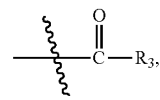

wherein, $R_3$ is a C1-C4 alkyl, preferably methyl, ethyl, n-propyl, isopropyl or isobutyl. Accordingly, in the present invention, $R_1$ is preferably

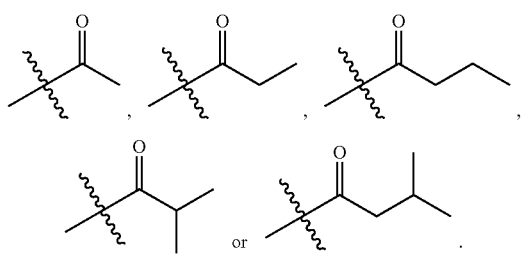

In the present invention, $R_2$ has the structure shown in formula III:

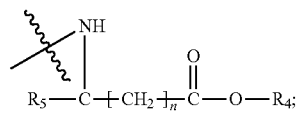

formula III in formula III, n=0, 1 or 2, $R_4$ is methyl or ethyl, $R_5$ is one of a hydrogen atom, a substituted or unsubstituted C1-C5 alkyl, a substituted or unsubstituted benzyl and a C4-C9 heterocycloalkyl.

In the present invention, the substituted or unsubstituted C1-C5 alkyl is preferably a C1-C5 alkyl, a C1-C5 hydroxyalkyl or a C3-C5 ester alkyl. In the present invention, the C1-C5 alkyl is preferably —CH$_2$CH(CH$_3$)$_2$ or —CH(CH$_3$)$_2$; the C1-C5 hydroxyalkyl is preferably —CH(OH)CH$_3$ or —CH$_2$OH; the C3-C5 ester alkyl is preferably —CH$_2$CH$_2$COOCH$_2$CH$_3$ or —CH$_2$COOCH$_2$CH$_3$.

In the present invention, the substituted benzyl is preferably hydroxybenzyl, specifically

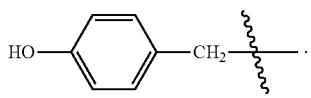 [SMILES: *Cc1ccc(O)cc1]

In the present invention, the C4-C9 heterocycloalkyl is preferably

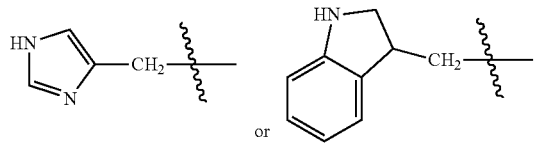

Accordingly, in the present invention, $R_2$ is preferably

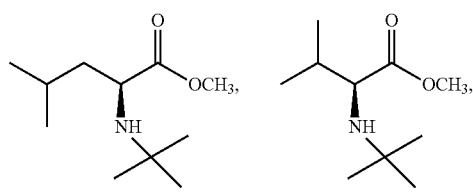

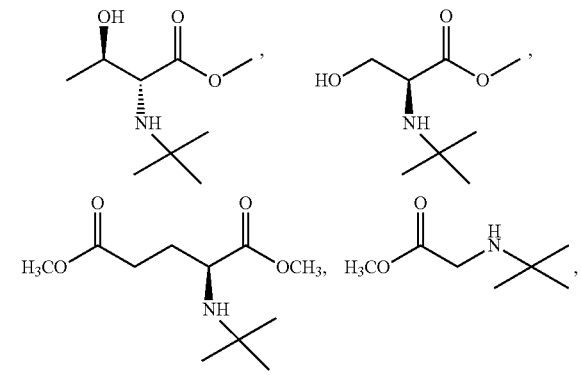

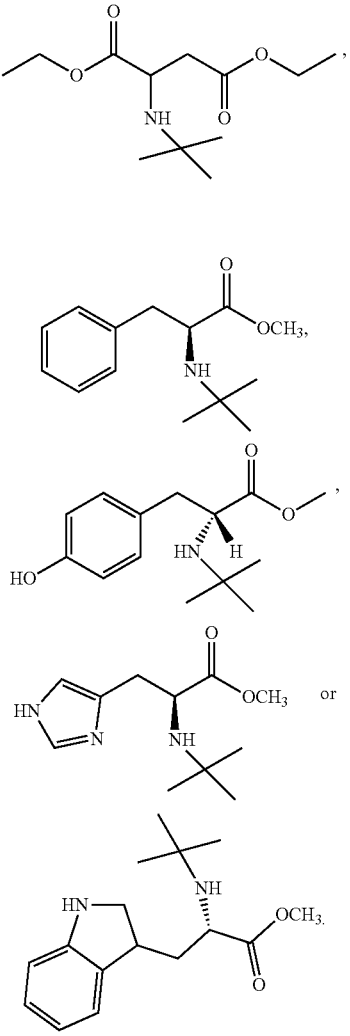

In the present invention, the panaxdiol-type ginsenoside derivative having the structure shown in formula I is preferably

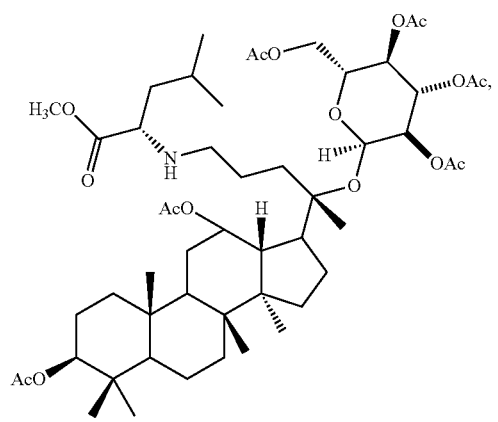
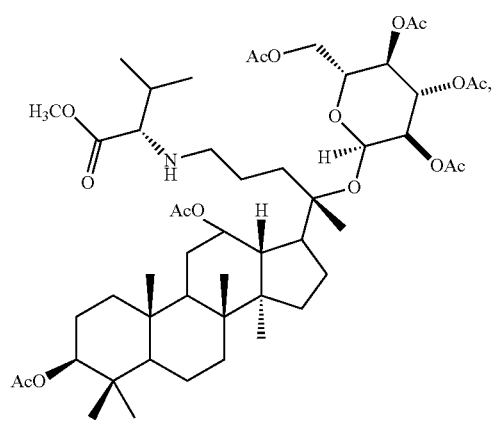
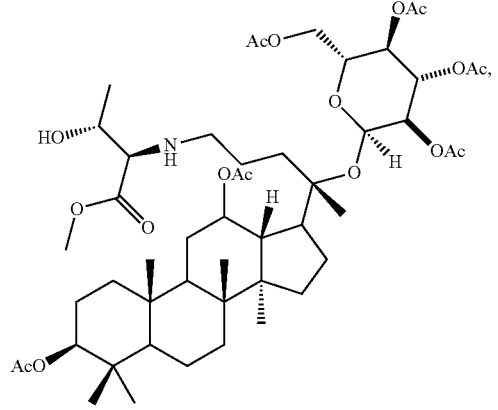
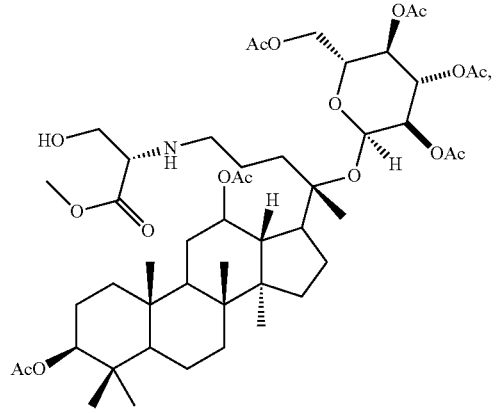
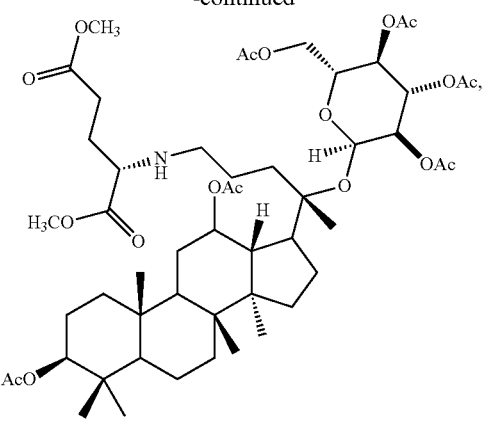
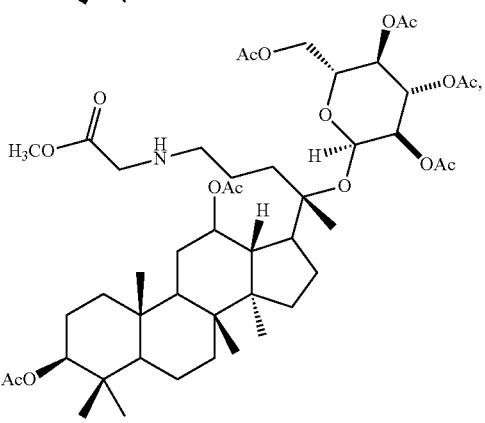
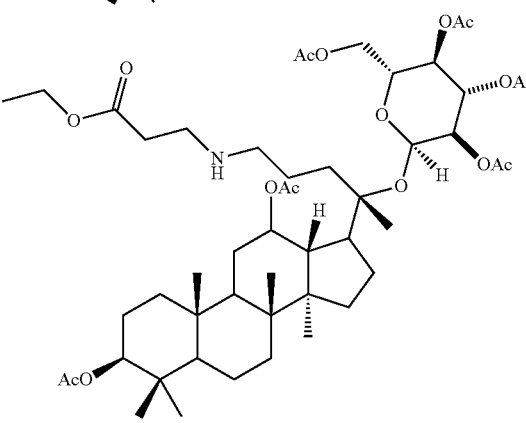
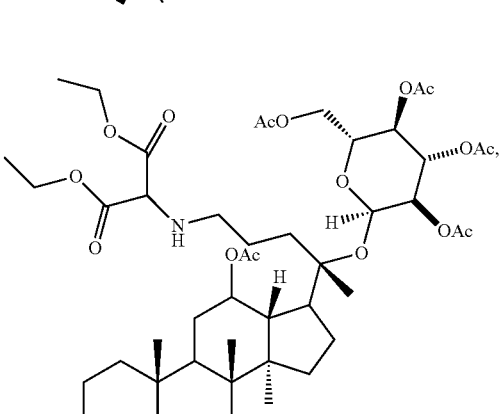

11
-continued
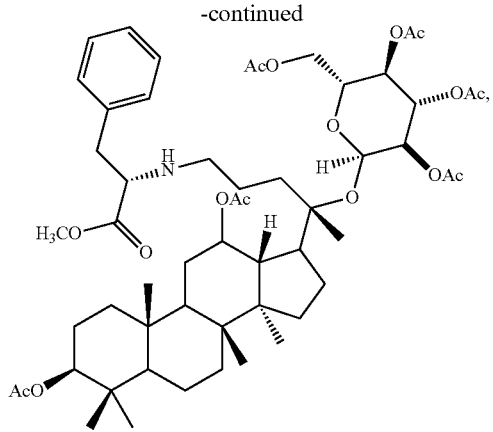
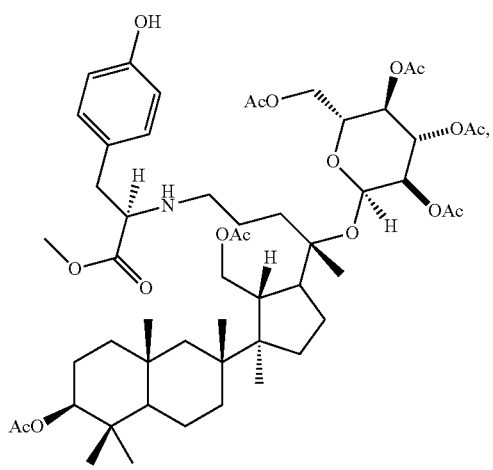
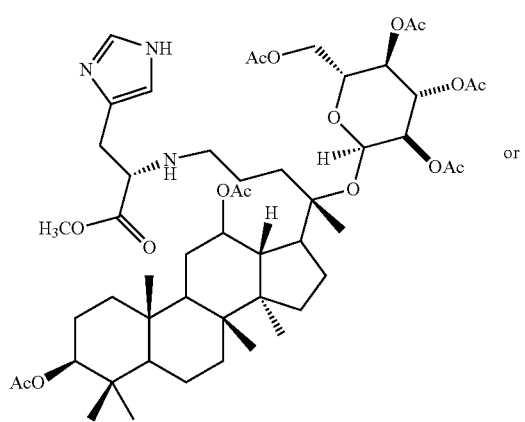
12
-continued
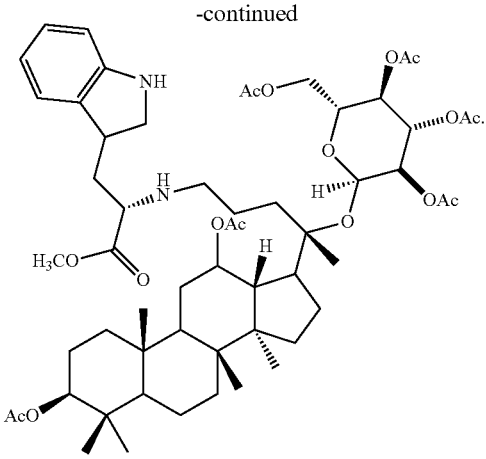
In the present invention, the panaxdiol-type ginsenoside derivative having the structure shown in formula II is preferably
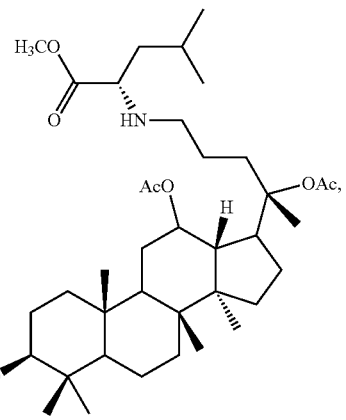
or
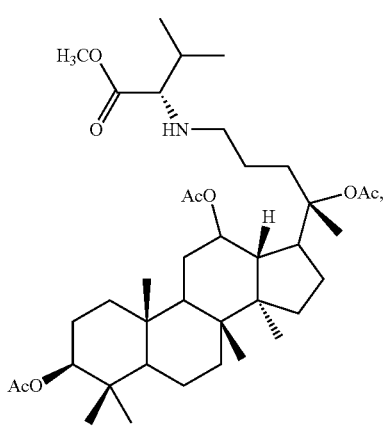

13
-continued
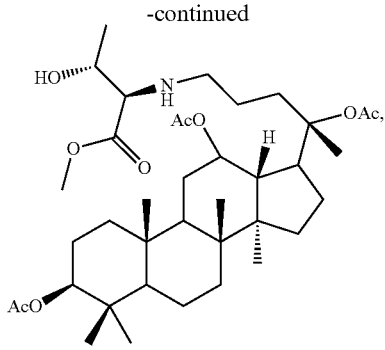
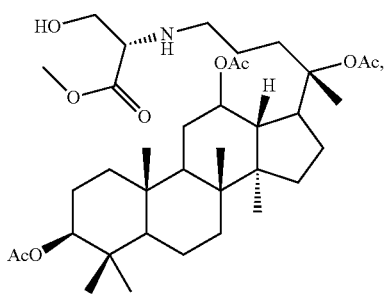
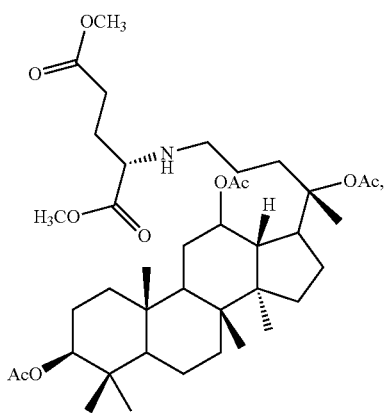
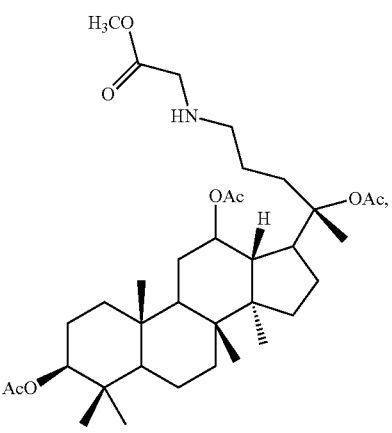
14
-continued
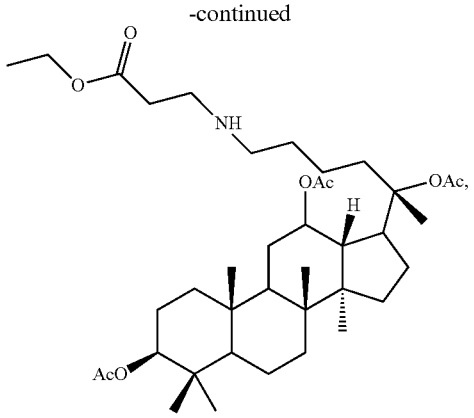
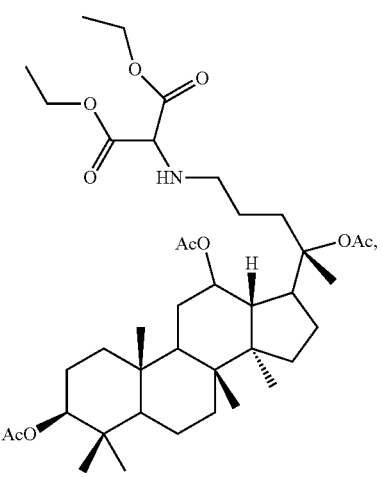
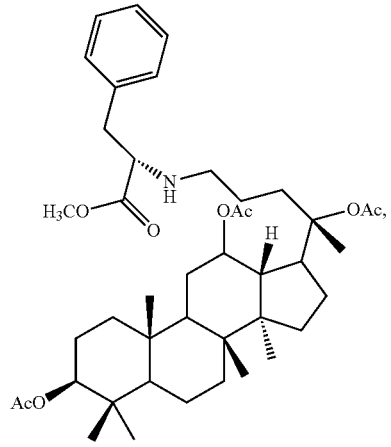

-continued

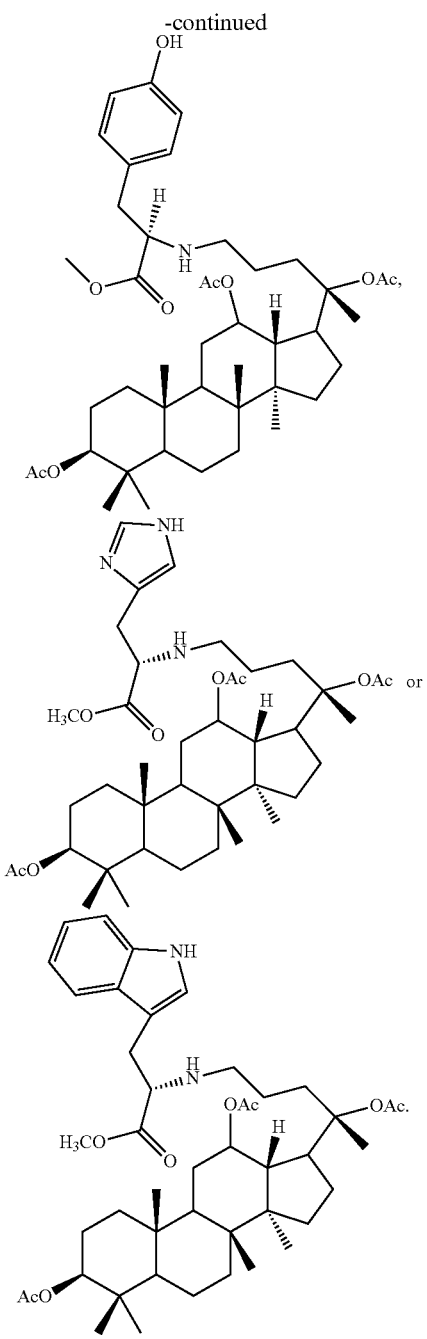

The present invention provides a preparation method of the panaxdiol-type ginsenoside derivative described in the above technical solution, comprising the following steps:

(1) subjecting a parent compound to a nucleophilic substitution reaction with an acid anhydride in the presence of an alkaline reagent to obtain a first intermediate product;

(2) subjecting the first intermediate product in step (1) to an oxidation reaction in the presence of an oxidizing agent and an organic solvent to obtain a second intermediate product;

(3) subjecting the second intermediate product in step (2) to a reductive amination reaction with an amino compound in the presence of an organic solvent and a reducing agent to obtain a panaxdiol-type ginsenoside derivative having the structure shown in formula I or formula II;

wherein the parent compound in step (1) has the structure shown in formula IV or formula V:

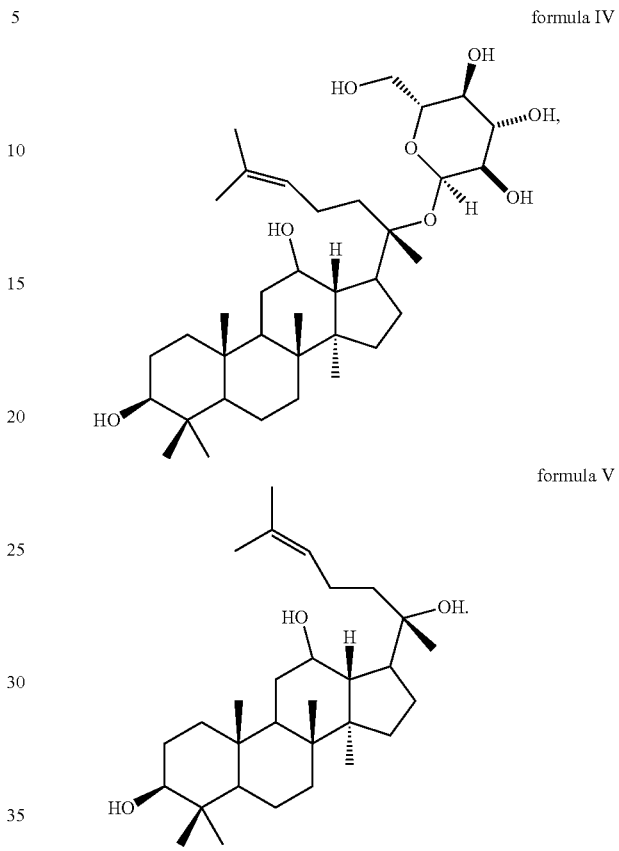

In the present invention, the parent compound having the structure shown in formula IV or formula V is subjected to a nucleophilic substitution reaction with an acid anhydride in the presence of an alkaline reagent to obtain a first intermediate product. In the present invention, the mass ratio of the parent compound:the acid anhydride:the alkaline reagent is preferably 1:(1-20):(1-20), more preferably 1:(4-15):(4-15), most preferably 1:(8-12):(8-12).

In the present invention, the type of the acid anhydride is not particularly limited, and an acid anhydride well known to those skilled in the art that can obtain the structure of $R_1$ can be used. In the present invention, the acid anhydride is preferably acetic anhydride, propionic anhydride, butyric anhydride, isobutyric anhydride or isovaleric anhydride.

In the present invention, the type of the alkaline agent is not particularly limited, and an organic alkaline compound, an inorganic alkaline compound and/or an alkali metal that are well known to those skilled in the art can be used.

In the present invention, the type of the organic alkaline compound is not particularly limited, and an organic alkaline compound well known to those skilled in the art can be used. In the present invention, the organic alkaline compound is preferably triethylamine, N,N-diisopropylethylamine, 4-dimethylaminopyridine, pyridine, N-methylmorpholine, tetramethylethylenediamine, potassium tert-butoxide, sodium methoxide, potassium ethoxide or sodium ethoxide.

In the present invention, the type of the inorganic alkaline compound is not particularly limited, and an inorganic alkaline compound well known to those skilled in the art can be used. In the present invention, the inorganic alkaline compound is preferably sodium hydroxide, potassium hydroxide, potassium carbonate, sodium carbonate or sodium hydride.

In the present invention, the type of the alkali metal is not particularly limited, and an alkali metal well known to those skilled in the art, such as sodium metal, can be used.

In the present invention, the temperature of the nucleophilic substitution reaction is preferably 0-100° C., more preferably 20-75° C., most preferably 35-60° C.; and the time of the nucleophilic substitution reaction is preferably 1-48 hours, more preferably 5-38 hours, most preferably 15-25 hours. In the present invention, the nucleophilic substitution reaction is preferably carried out under stirring. In the present invention, the stirring rate is preferably 800-1200 rpm, more preferably 900-1100 rpm. In the present invention, the method of the stirring is not particularly limited, and a stirring method well known to those skilled in the art can be used. Magnetic stirring is preferably used in the present invention.

In the present invention, preferably, after the completion of the nucleophilic substitution reaction, the obtained product is subjected to a post-treatment to obtain the first intermediate product. In the present invention, the post-processing preferably comprises the following steps:

After the nucleophilic substitution reaction, distillation is carried out under reduced pressure, and a crude product is obtained; the crude product is purified by silica gel column chromatography to obtain the first intermediate product.

In the present invention, the specific operation steps and reagents used in the silica gel column chromatography are not particularly limited, and silica gel column chromatography well known to those skilled in the art can be used. In the present invention, the crude product is preferably mixed with ethyl acetate, and the mixture is used for column chromatography after silica gel mixing. In the present invention, the mass ratio of the crude product to ethyl acetate is preferably 1:(1-10), more preferably 1:(3-8), and most preferably 1:(4-6). In the present invention, ethyl acetate and n-hexane are preferably used as an eluent, and the volume ratio of ethyl acetate to n-hexane in the eluent is preferably 1:(1-10), more preferably 1:(3-8), most preferably 1:(4-6).

In the present invention, after a first intermediate product is obtained, the first intermediate product is subjected to an oxidization reaction in the presence of an oxidizing agent and an organic solvent to obtain a second intermediate product. In the present invention, the oxidation reaction is specifically:

subjecting the first intermediate product to a primary oxidation reaction in the presence of a first oxidizing agent and an organic solvent to obtain a precursor of the second intermediate product;

subjecting the precursor of the second intermediate product to a secondary oxidation reaction in the presence of a second oxidizing agent and an organic solvent to obtain the second intermediate product.

In the present invention, the first intermediate product is subjected to a primary oxidation reaction in the presence of a first oxidizing agent and an organic solvent to obtain a second intermediate product precursor. In the present invention, the mass ratio of the first intermediate product:the first oxidizing agent:the organic solvent is preferably 1:(0.1-0.5):(5-10), more preferably 1:(0.2-0.4):(6-8).

In the present invention, the first oxidizing agent is preferably hydrogen peroxide, hypochlorous acid, calcium hypochlorite, acetone peroxide or meta-chloroperbenzoic acid.

In the present invention, the type of the organic solvent required for carrying out the primary oxidation reaction of the present invention is not particularly limited, and a polar organic solvent or non-polar organic solvent well known to those skilled in the art that is compatible with the first intermediate product and the first oxidizing agent, such as pyridine, N-methylpyrrolidone, chloroform, dichloromethane, carbon tetrachloride, tetrahydrofuran or 1,4-dioxane, can be used.

In the present invention, the temperature of the primary oxidation reaction is preferably 10-80° C., more preferably 15-55° C., and most preferably 20-35° C.; specifically, in the embodiments of the present invention, the primary oxidation reaction is carried out at room temperature without heating or cooling the reaction system. In the present invention, the time of the primary oxidation reaction is preferably 1-10 hours, more preferably 3-8 hours, and most preferably 4-6 hours.

In the present invention, preferably, after the completion of the primary oxidation reaction, the obtained product is subjected to a post-treatment to obtain a second intermediate product precursor. In the present invention, the post-treatment preferably comprises the following steps:

adding water to the material obtained after the primary oxidation reaction and stirring, filtering, removing the solvent, obtaining a crude product; purifying the crude product by silica gel column chromatography to obtain a second intermediate product.

In the present invention, the mass ratio of the material obtained after the primary oxidation reaction to water is preferably 1:(1-100), more preferably 1:(8-70), and most preferably 1:(20-40). In the present invention, the stirring rate is preferably 800-1200 rpm, more preferably 900-1100 rpm; and the stirring time is preferably 1-10 hours, more preferably 3-8 hours, and most preferably 4-6 hours. In the present invention, the method of the stirring is not particularly limited, and a stirring method well known to those skilled in the art can be used. Magnetic stirring is preferably used in the present invention. In the present invention, the filtering is not particularly limited, and a technical solution of filtering well known to those skilled in the art can be used. In the present invention, the method for removing the solvent is not particularly limited, and a technical solution of removing the solvent well known to those skilled in the art can be used. Distillation under reduced pressure is preferably used to remove the solvent in the present invention.

In the present invention, the specific operation steps and reagents used in the silica gel column chromatography are not particularly limited, and silica gel column chromatography well known to those skilled in the art can be used. In the present invention, the crude product is preferably mixed with ethyl acetate, and the mixture is used for column chromatography after silica gel mixing. In the present invention, the mass ratio of the crude product to ethyl acetate is preferably 1:(1-10), more preferably 1:(3-8), and most preferably 1:(4-6). In the present invention, ethyl acetate and n-hexane are preferably used as an eluent, and the volume ratio of ethyl acetate to n-hexane in the eluent is preferably 1:(1-10), more preferably 1:(3-8), most preferably 1:(4-6).

In the present invention, after the precursor of the second intermediate product is obtained, the precursor of the second intermediate product is subjected to a secondary oxidation reaction in the presence of a second oxidizing agent and an organic solvent to obtain the second intermediate product. In the present invention, the mass ratio of the precursor of the second intermediate product:the second oxidizing agent:the organic solvent is preferably 1:(0.1-0.3):(5-10), more preferably 1:(0.15-0.25):(6-8).

In the present invention, the second oxidizing agent is preferably potassium permanganate, manganese dioxide, periodic acid or Sarrett reagent.

In the present invention, the type of the organic solvent required for carrying out the secondary oxidation reaction is not particularly limited, and a polar organic solvent or non-polar organic solvent well known to those skilled in the art that is compatible with the precursor of the second intermediate product and the second oxidizing agent, such as chloroform, dichloromethane, carbon tetrachloride, acetonitrile, tetrahydrofuran or 1,4-dioxane, can be used.

In the present invention, the temperature of the secondary oxidation reaction is preferably 10-100° C., more preferably 15-65° C., most preferably 20-45° C.; specifically, in the embodiments of the present invention, the secondary oxidation reaction is carried out at room temperature without heating or cooling the reaction system. In the present invention, the time of the secondary oxidation reaction is preferably 1-10 hours, more preferably 3-8 hours, and most preferably 4-6 hours.

In the present invention, preferably, after the completion of the secondary oxidation reaction, the obtained product is subjected to a post-treatment to obtain the second intermediate product. In the present invention, the post-treatment preferably comprises the following steps:

extracting the material obtained after the secondary oxidation reaction with an organic solvent, washing, removing the solvent, obtaining a crude product; purifying the crude product by silica gel column chromatography to obtain the second intermediate product.

In the present invention, the mass ratio of the material obtained after the secondary oxidation reaction to an extractant is preferably 1:(10-30), more preferably 1:(15-25), and most preferably 1:(18-22). In the present invention, the extractant is preferably ethyl acetate, chloroform, dichloromethane or carbon tetrachloride. In the present invention, the extraction is preferably carried out for 2-4 times. In the present invention, specifically, the organic phase obtained after the extraction is washed.

In the present invention, the washing is not particularly limited, and a technical solution of washing well known to those skilled in the art can be used. In the present invention, preferably, the material obtained after extraction is washed successively with an alkali solution and a sodium chloride solution. In the present invention, the volume ratio of the material obtained after extraction to the alkali solution or the sodium chloride solution is preferably 1:(1-10), more preferably 1:(3-8), and most preferably 1:(4-6). In the present invention, the type of the alkali solution is not particularly limited, and an alkali solution well known to those skilled in the art, such as sodium bicarbonate solution, can be used. In the present invention, the concentrations of the alkali solution and the sodium chloride solution is not particularly limited, and concentrations of the solutions suitable for washing well known to those skilled in the art can be used. In the embodiments of the present invention, the washing is carried out specifically using a saturated alkali solution and a saturated sodium chloride solution. In the present invention, the material obtained after the extraction is preferably washed with an alkali solution for 3-5 times, and then washed with a sodium chloride solution for 3-5 times. In the present invention, the method for removing the solvent is not particularly limited, and a technical solution for removing the solvent well known to those skilled in the art can be used. Distillation under reduced pressure is preferably used in the present invention.

In the present invention, the specific operation steps and reagents used in the silica gel column chromatography are not particularly limited, and silica gel column chromatography well known to those skilled in the art can be used. In the present invention, the crude product is preferably mixed with ethyl acetate, and the mixture is used for column chromatography after silica gel mixing. In the present invention, the mass ratio of the crude product to ethyl acetate is preferably 1:(1-10), more preferably 1:(3-8), and most preferably 1:(4-6). In the present invention, ethyl acetate and n-hexane are preferably used as an eluent, and the volume ratio of ethyl acetate to n-hexane in the eluent is preferably 1:(1-10), more preferably 1:(3-8), most preferably 1:(4-6).

In the present invention, after the second intermediate product is obtained, the second intermediate product is subjected to a reductive amination reaction with an amino compound in the presence of an organic solvent and a reducing agent to obtain a panaxdiol-type ginsenoside derivative having the structure shown in formula I or formula II; in the present invention, the mass ratio of the second intermediate product to the amino compound and the reducing agent is preferably 1:(1-100):(5-10), more preferably 1:(8-70):(6-9), and even more preferably 1:(20-50):(7-8).

In the present invention, the amino compound is preferably L-leucine methyl ester hydrochloride, L-valine methyl ester hydrochloride, L-threonine methyl ester hydrochloride, L-serine methyl ester hydrochloride, L-glutamic acid dimethyl ester hydrochloride, glycine methyl ester hydrochloride, β-alanine ethyl ester hydrochloride, diethyl aminomalonate hydrochloride, L-phenylalanine methyl ester hydrochloride, L-tyrosine methyl ester, L-histidine methyl ester hydrochloride or L-tryptophan methyl ester hydrochloride.

In the present invention, the reducing agent is preferably sodium borohydride, sodium cyanoborohydride or sodium triacetylborohydride.

In the present invention, the type of the organic solvent required for carrying out the reductive amination reaction is not particularly limited, and a polar organic solvent or non-polar organic solvent well known to those skilled in the art that is compatible with the second intermediate product, the amino compound and the reducing agent such as methanol, ethyl acetate, chloroform, dichloromethane and carbon tetrachloride, can be used.

In the present invention, the reducing agent is preferably mixed with the second intermediate product, the amino compound and the organic solvent within the temperature range of −2-2° C. In the present invention, the method for controlling the temperature for mixing the reducing agent with the second intermediate product, the amino compound and the organic solvent is not particularly limited, and a method for controlling temperature well known to those skilled in the art can be used. In the embodiments of the present invention, specifically, the reducing agent is mixed with the second intermediate product, the amino compound and the organic solvent in the condition of ice water bath. In the present invention, the reducing agent is preferably mixed with the second intermediate product, the amino compound and the organic solvent under stirring. In the present invention, the rate of stirring is preferably 800-1200 rpm, more preferably 900-1100 rpm. In the present invention, the method of stirring is not particularly limited, and a stirring method well known to those skilled in the art can be used. Magnetic stirring is preferably used in the present invention.

In the present invention, the temperature of the reductive amination reaction is preferably −10-80° C., more preferably 0-55° C., and most preferably 20-35° C.; specifically, in the embodiments of the present invention, the reductive amination reaction is carried out at room temperature without heating or cooling the reaction system. In the present invention, the time of the reductive amination reaction is preferably 1-48 hours, more preferably 8-32 hours, and most preferably 13-20 hours.

In the present invention, preferably, after the completion of the reductive amination reaction, the obtained product is subjected to a post-treatment to obtain a panaxdiol-type ginsenoside derivative having a structure as shown in formula I or formula II. In the present invention, the post-treatment preferably comprises the following steps:

extracting the material obtained after the reductive amination reaction with an organic solvent, washing, removing the solvent, obtaining a crude product; purifying the crude product by silica gel column chromatography to obtain the panaxdiol-type ginsenoside derivative having a structure as shown in formula I or formula II.

In the present invention, the mass ratio of the material obtained after the reductive amination reaction to an extractant is preferably 1:(1-50), more preferably 1:(8-40), and most preferably 1:(15-25). In the present invention, the extractant is preferably ethyl acetate, chloroform, dichloromethane or carbon tetrachloride. In the present invention, the extraction is preferably carried out for 2-4 times. In the present invention, specifically, the organic phase obtained after the extraction is washed.

In the present invention, the washing is not particularly limited, and a technical solution of washing well known to those skilled in the art can be used. In the present invention, preferably, the material obtained after extraction is washed with a sodium chloride solution. In the present invention, the concentration of the sodium chloride solution is not particularly limited, and concentrations of the solution suitable for washing well known to those skilled in the art can be used. In the embodiments of the present invention, the washing is carried out specifically using a saturated sodium chloride solution. In the present invention, the volume ratio of the material obtained after the extraction to the sodium chloride solution is preferably 1:(1-30), more preferably 1:(5-23), most preferably 1:(10-15). In the present invention, the washing is preferably carried out for 3-5 times. In the present invention, the method for removing the solvent is not particularly limited, and a technical solution for removing the solvent well known to those skilled in the art can be used. Distillation under reduced pressure is preferably used in the present invention.

In the present invention, the specific operation steps and reagents used in the silica gel column chromatography are not particularly limited, and silica gel column chromatography well known to those skilled in the art can be used. In the present invention, the crude product is preferably mixed with ethyl acetate, and the mixture is used for column chromatography after silica gel mixing. In the present invention, the mass ratio of the crude product to ethyl acetate is preferably 1:(1-10), more preferably 1:(3-8), and most preferably 1:(4-6). In the present invention, ethyl acetate and n-hexane are preferably used as an eluent, and the volume ratio of ethyl acetate to n-hexane in the eluent is preferably 1:(1-10), more preferably 1:(3-8), most preferably 1:(4-6).

The present invention provides the use of the panaxdiol-type ginsenoside derivative of the above technical solution or use of the panaxdiol-type ginsenoside derivative obtained by the preparation method of the above technical solution in the preparation of a medicament for preventing and treating atherosclerosis. In the present invention, the medicament for preventing and treating atherosclerosis preferably comprises an active ingredient and an adjuvant. In the present invention, the active ingredient of the medicament for preventing and treating atherosclerosis is the panaxdiol-type ginsenoside derivative of the above technical solution of the present invention or the panaxdiol-type ginsenoside derivative obtained by the preparation method of the above technical solution. In the present invention, the type of the adjuvant is not particularly limited, and an adjuvant well known to those skilled in the art can be used. In the present invention, the ratio of the active ingredient to the adjuvant is not particularly limited, and the ratio of the active ingredient to the adjuvant can be determined according to actual conditions. In the present invention, the dosage form and dosage of the medicament for preventing and treating atherosclerosis are not particularly limited, and the dosage form and dosage of the medicament for preventing and treating atherosclerosis can be determined according to actual needs.

The technical solutions in the present invention will be clearly and completely described below in combination with the examples of the present invention. It is apparent that the described examples are only a part but not all of the examples of the present invention. All other examples obtained by those skilled in the art based on the examples of the present invention without making creative efforts are within the scope of protection of the present invention.

Example 1

1 g (16 mmol) of a compound having the structure shown in Formula IV was mixed with 10 mL of acetic anhydride and 10 mL of pyridine, and a nucleophilic substitution reaction is carried out for 3 hours under the condition of magnetic stirring at 900 rpm and 40° C.; the obtained system was distilled under reduced pressure, the obtained crude product was mixed with 6 mL of ethyl acetate, and the mixture was used for a column chromatography after silica gel mixing. A mixture of ethyl acetate and n-hexane was used as an eluent (the volume ratio of ethyl acetate to n-hexane was 1:5), 1.3 g of compound 1 was obtained as a white solid, yield: 90%. The structure of the compound 1 iS:

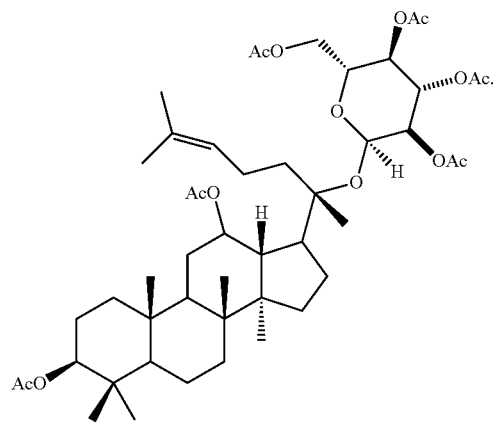

Example 2

1 g (11 mmol) of compound 1 prepared in example 1, 5 mL of dichloromethane and 0.2 g (11 mmol) of meta-chloroperoxybenzoic acid were mixed, a primary oxidation reaction was carried out at room temperature for 1 hour; 25 mL of water was added to the material obtained after the primary oxidation reaction, magnetic stirring was carried out at 1100 rpm for 1 hour, a white solid was precipitated, filtered to obtain clear solution, the clear solution was distilled under reduced pressure to remove solvent, the obtained crude product was mixed with 8 mL of ethyl acetate, the mixture was used for a column chromatography after silica gel mixing. A mixture of ethyl acetate and n-hexane was used as an eluent (the volume ratio of ethyl acetate to n-hexane was 1:8), 0.87 g of compound 2 was obtained as a white solid, yield: 90%. The structure of the compound 2 is:

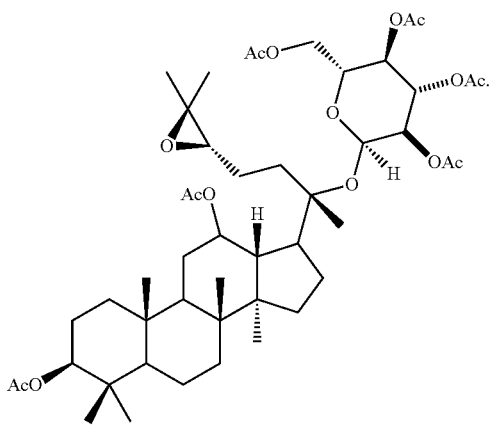

Example 3

0.8 g (9 mmol) of compound 2 prepared in example 2, 5 mL of tetrahydrofuran and 0.32 g (14 mmol) of periodic acid were mixed, a secondary oxidation reaction was carried out at room temperature for 2 hours; the material obtained after the secondary oxidation reaction was extracted with ethyl acetate for three times (the volume of ethyl acetate required for each time of extraction was 40 mL), then was washed with saturated sodium bicarbonate solution and saturated sodium chloride solution successively, four times for each solution to obtain a clear solution (the volume of saturated sodium bicarbonate solution required for each time of washing was 50 mL, the volume of saturated sodium chloride solution required for each time of washing was 60 mL), the clear solution was distilled under reduced pressure to remove solvent, the obtained crude product was mixed with 4 mL of ethyl acetate, the mixture was used for a column chromatography after silica gel mixing. A mixture of ethyl acetate and n-hexane was used as an eluent (the volume ratio of ethyl acetate to n-hexane was 1:4), 0.73 g of compound 3 was obtained as a white solid, yield: 92%. The structure of the compound 3 is:

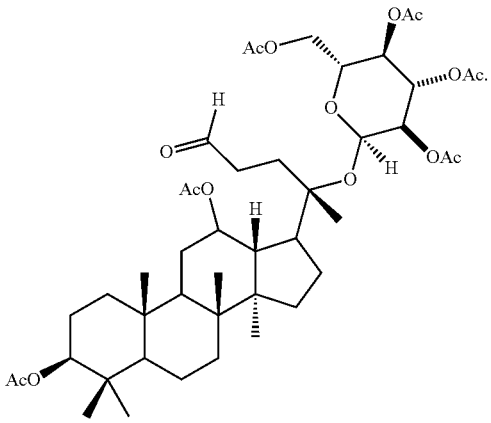

Example 4

0.05 g (0.6 mmol) of compound 3 prepared in example 3 was mixed with 0.013 g (0.7 mmol) of L-leucine methyl ester hydrochloride and 2 mL of methanol, 0.05 g (8 mmol) of sodium cyanoborohydride was added under the conditions of ice bath and magnetic stirring at 1000 rpm, and a reductive amination reaction was carried out at room temperature for 1 hour; the material obtained after the reductive amination reaction was extracted with ethyl acetate for three times (the volume of ethyl acetate required for each time of extraction was 10 mL), then was washed with saturated sodium chloride solution for four times to obtain a clear solution (the volume of saturated sodium chloride solution required for each time of washing was 30 mL), the clear solution was distilled under reduced pressure to remove solvent, the obtained crude product was mixed with 6 mL of ethyl acetate, the mixture was used for a column chromatography after silica gel mixing. A mixture of ethyl acetate and n-hexane was used as an eluent (the volume ratio of ethyl acetate to n-hexane was 1:7), 0.03 g of target compound 4 was obtained as a white solid, yield: 52%. The structure of the target compound 4 is:

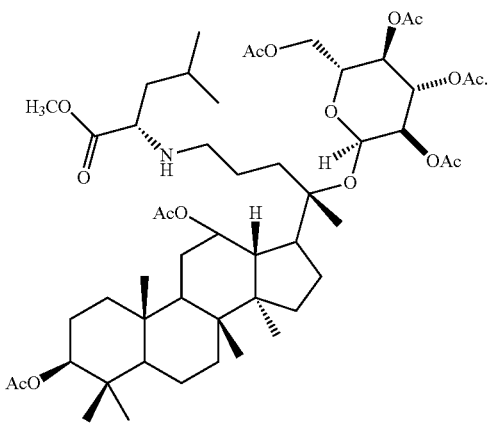

$^1$H NMR (600 MHz, cdcl3) δ 5.90 (t, 1H), 5.70 (dd, 1H), 5.11 (t, 1H), 4.87 (m, 2H), 4.55 (m, 1H), 4.41 (m, 1H), 4.29 (m, 1H), 4.19 (m, 1H), 3.62 (d, 2H), 3.05 (m, 1H), 2.55 (m, 2H), 2.283 (m, 1H), 2.062 (m, 2H), 2.00 (ddd, 18H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.94 (s, 3H), 0.92 (s, 3H), 0.85 (m, 1H), 0.84 (s, 3H), 0.82 (s, 3H).

Example 5

0.05 g (0.6 mmol) of compound 3 prepared in example 3 was mixed with 0.012 g (0.7 mmol) of L-valine methyl ester hydrochloride and 2 mL of ethyl acetate, 0.05 g (8 mmol) of sodium borohydride was added under the conditions of ice bath and magnetic stirring at 800 rpm, and a reductive amination reaction was carried out at room temperature for 3 hours; the material obtained after the reductive amination reaction was extracted with ethyl acetate for three times (the volume of ethyl acetate required for each time of extraction was 100 mL), then was washed with saturated sodium chloride solution for four times to obtain a clear solution (the volume of saturated sodium chloride solution required for each time of washing was 50 mL), the clear solution was distilled under reduced pressure to remove solvent, the obtained crude product was mixed with 10 mL of ethyl acetate, the mixture was used for a column chromatography after silica gel mixing. A mixture of ethyl acetate and n-hexane was used as an eluent (the volume ratio of ethyl acetate to n-hexane was 1:6), 0.03 g of target compound 5 was obtained as a white solid, yield: 60%. The structure of the target compound 5 is:

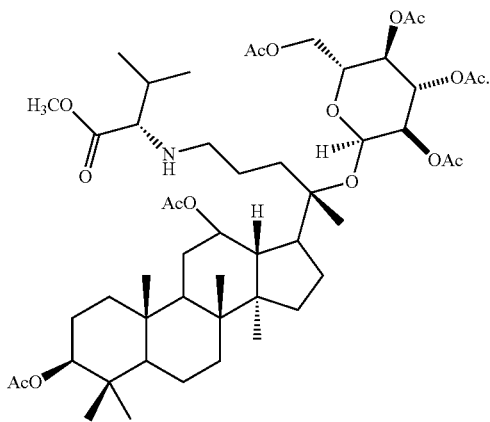

$^1$H NMR (600 MHz, cdcl3) δ 6.98 (t, 1H), 5.22 (m, 3H), 4.86 (m, 1H), 4.69 (dd, 1H), 4.50 (m, 1H), 4.42 (m, 2H), 4.27 (m, 1H), 4.01 (m, 1H), 3.66 (s, 3H), 2.67 (m, 1H), 2.58 (m, 2H), 2.33 (m, 1H), 2.283 (m, 1H), 2.062 (m, 2H), 2.00 (ddd, 18H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.98 (s, 3H), 0.94 (s, 3H), 0.96 (s, 3H), 0.92 (s, 3H), 0.85 (m, 1H), 0.84 (s, 3H), 0.82 (s, 3H).

Example 6

0.05 g (0.6 mmol) of compound 3 prepared in example 3 was mixed with 0.012 g (0.7 mmol) of L-threonine methyl ester hydrochloride and 2 mL of chloroform, 0.05 g (8 mmol) of sodium triacetylborohydride was added under the conditions of ice bath and magnetic stirring at 900 rpm, and a reductive amination reaction was carried out at room temperature for 6 hours; the material obtained after the reductive amination reaction was extracted with ethyl acetate for three times (the volume of ethyl acetate required for each time of extraction was 90 mL), then was washed with saturated sodium chloride solution for four times to obtain a clear solution (the volume of saturated sodium chloride solution required for each time of washing was 10 mL), the clear solution was distilled under reduced pressure to remove solvent, the obtained crude product was mixed with 1 mL of ethyl acetate, the mixture was used for a column chromatography after silica gel mixing. A mixture of ethyl acetate and n-hexane was used as an eluent (the volume ratio of ethyl acetate to n-hexane was 1:1), 0.02 g of target compound 6 was obtained as a white solid, yield: 40%. The structure of the target compound 6 is:

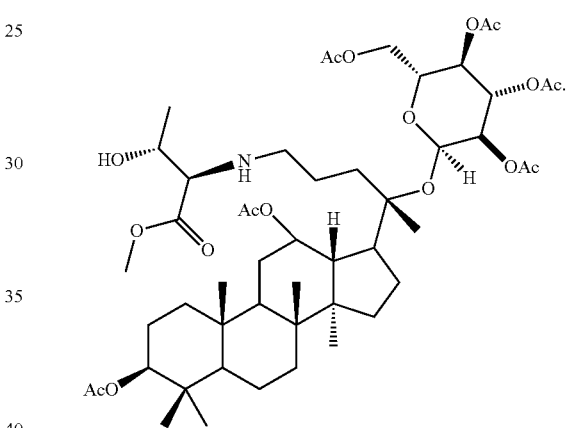

$^1$H NMR (600 MHz, cdcl3) δ 5.66 (t, 1H), 5.37 (m, 2H), 5.03 (m, 2H), 4.42 (s, 2H), 4.28 (m, 1H), 4.09 (m, 1H), 3.77 (m, 1H), 3.66 (s, 3H), 2.74 (m, 1H), 2.57 (m, 2H), 2.283 (m, 1H), 2.062 (m, 2H), 12.00 (ddd, 18H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.18 (s, 3H), 1.11 (s, 3H), 1.09 (m, 1H), 1.03 (m, 1H), 0.94 (s, 3H), 0.92 (s, 3H), 0.85 (m, 1H), 0.84 (s, 3H), 0.82 (s, 3H).

Example 7

0.05 g (0.6 mmol) of compound 3 prepared in example 3 was mixed with 0.011 g (0.7 mmol) of L-serine methyl ester hydrochloride and 2 mL of dichloromethane, 0.05 g (8 mmol) of sodium cyanoborohydride was added under the conditions of ice bath and magnetic stirring at 1000 rpm, and a reductive amination reaction was carried out at room temperature for 9 hours; the material obtained after the reductive amination reaction was extracted with ethyl acetate for three times (the volume of ethyl acetate required for each time of extraction was 20 mL), then was washed with saturated sodium chloride solution for four times to obtain a clear solution (the volume of saturated sodium chloride solution required for each time of washing was 90 mL), the clear solution was distilled under reduced pressure to remove solvent, the obtained crude product was mixed with 2 mL of ethyl acetate, the mixture was used for a column chromatography after silica gel mixing. A mixture of ethyl acetate and n-hexane was used as an eluent (the volume ratio of ethyl acetate to n-hexane was 1:2), 0.02 g of target compound 7 was obtained as a white solid, yield: 40%. The structure of the target compound 7 is:

of ethyl acetate and n-hexane was used as an eluent (the volume ratio of ethyl acetate to n-hexane was 1:3), 0.03 g of target compound 8 was obtained as a white solid, yield: 55%. The structure of the target compound 8 is:

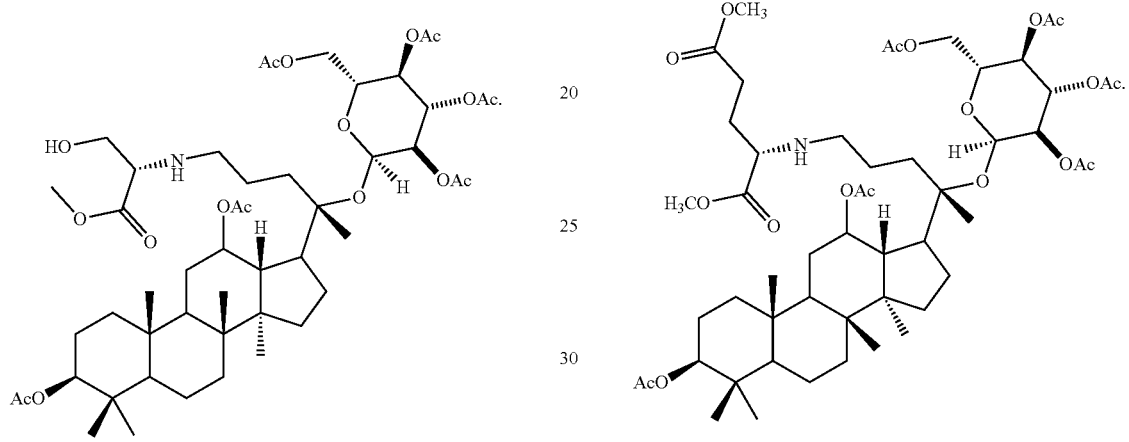

¹H NMR (600 MHz, cdcl3) δ 6.26 (t, 1H), 5.37 (t, 1H), 5.29 (m, 1H), 4.95 (m, 2H), 4.45 (m, 1H), 4.28 (m, 2H), 4.15 (m, 2H), 3.77 (m, 1H), 3.66 (s, 3H), 3.25 (t, 1H), 2.57 (m, 2H), 2.283 (m, 1H), 2.062 (m, 2H), 2.00 (ddd, 18H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.94 (s, 3H), 0.92 (s, 3H), 0.85 (m, 1H), 0.84 (s, 3H), 0.82 (s, 3H).

¹H NMR (600 MHz, cdcl3) δ 6.68 (t, 1H), 5.63 (t, 1H), 5.06 (m, 1H), 4.95 (t, 2H), 4.82 (m, 1H), 4.55 (m, 2H), 4.26 (t, 1H), 3.99 (m, 1H), 3.66 (s, 3H), 3.60 (s, 3H), 3.55 (t, 1H), 2.57 (m, 2H), 2.35 (m, 2H), 2.28 (m, 1H), 2.22 (m, 1H), 2.09 (m, 1H), 2.062 (m, 2H), 2.00 (ddd, 18H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.94 (s, 3H), 0.92 (s, 3H), 0.85 (m, 1H), 0.84 (s, 3H), 0.82 (s, 3H).

Example 8

0.05 g (0.6 mmol) of compound 3 prepared in example 3 was mixed with 0.017 g (0.7 mmol) of L-glutamic acid dimethyl ester hydrochloride and 2 mL of carbon tetrachloride, 0.05 g (8 mmol) of sodium cyanoborohydride was added under the conditions of ice bath and magnetic stirring at 1100 rpm, and a reductive amination reaction was carried out at room temperature for 1 hour; the material obtained after the reductive amination reaction was extracted with ethyl acetate for three times (the volume of ethyl acetate required for each time of extraction was 30 mL), then was washed with saturated sodium chloride solution for four times to obtain a clear solution (the volume of saturated sodium chloride solution required for each time of washing was 80 mL), the clear solution was distilled under reduced pressure to remove solvent, the obtained crude product was mixed with 3 mL of ethyl acetate, the mixture was used for a column chromatography after silica gel mixing. A mixture Example 9

0.05 g (0.6 mmol) of compound 3 prepared in example 3 was mixed with 0.009 g (0.7 mmol) of glycine methyl ester hydrochlorideand 2 mL of methanol, 0.05 g (8 mmol) of sodium cyanoborohydride was added under the conditions of ice bath and magnetic stirring at 1200 rpm, and a reductive amination reaction was carried out at room temperature for 1 hour; the material obtained after the reductive amination reaction was extracted with ethyl acetate for three times (the volume of ethyl acetate required for each time of extraction was 40 mL), then was washed with saturated sodium chloride solution for four times to obtain a clear solution (the volume of saturated sodium chloride solution required for each time of washing was 70 mL), the clear solution was distilled under reduced pressure to remove solvent, the obtained crude product was mixed with 4 mL of ethyl acetate, the mixture was used for a column chromatography after silica gel mixing. A mixture of ethyl acetate and n-hexane was used as an eluent (the volume ratio of ethyl acetate to n-hexane was 1:4), 0.03 g of target compound 9 was obtained as a white solid, yield: 60%. The structure of the target compound 9 is:

ethyl acetate to n-hexane was 1:5), 0.03 g of target compound 10 was obtained as a white solid, yield: 60%. The structure of the target compound 10 is:

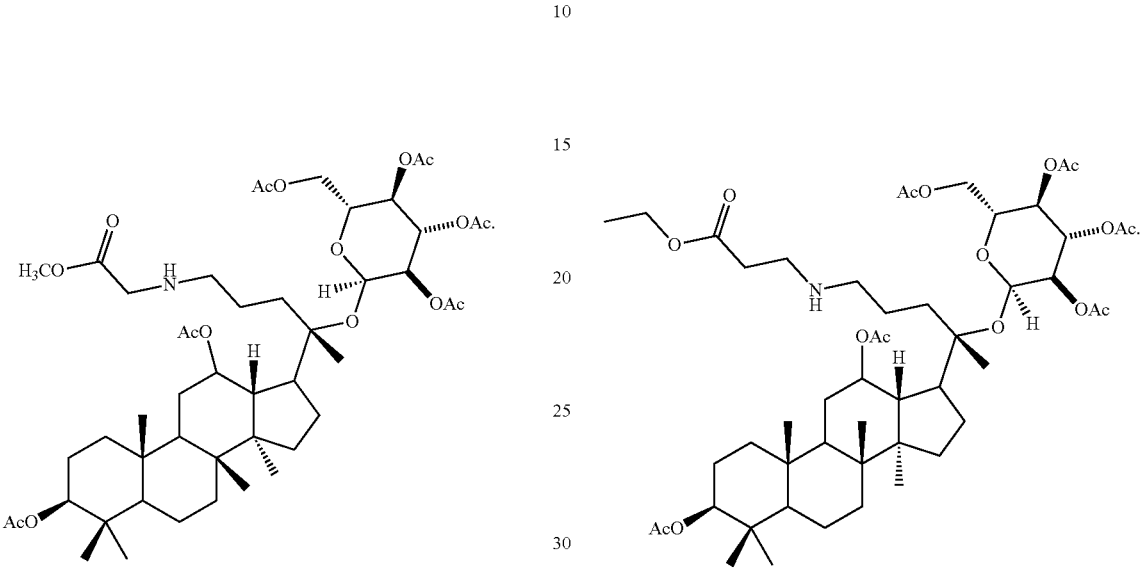

1H NMR (600 MHz, cdcl3) δ 6.66 (t, 1H), 4.95-4.82 (m, 5H), 4.55 (m, 1H), 4.44 (m, 1H), 4.28 (t, 1H), 4.01 (m, 1H), 3.72 (s, 3H), 3.62 (d, 2H), 2.57 (m, 2H), 2.44 (m, 1H), 2.283 (m, 1H), 2.062 (m, 2H), 2.00 (ddd, 18H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.94 (s, 3H), 0.92 (s, 3H), 0.85 (m, 1H), 0.84 (s, 3H), 0.82 (s, 3H).

$^1$H NMR (600 MHz, cdcl$_3$) δ 5.16 (t, 1H), 4.97 (t, Hz, 1H), 4.89 (dd, 1H), 4.66 (d, 1H), 4.10-4.06 (m, 1H), 4.04 (dd, J=12.3, 5.3 Hz, 1H), 3.60 (ddd, 1H), 2.70 (ddd, 1H), 2.37-2.29 (m, 1H), 2.283 (m, 1H), 2.14-2.08 (m, 2H), 2.062 (m, 2H), 2.00 (ddd, 18H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.07 (m, 3H), 1.03 (m, 1H), 0.94 (s, 3H), 0.92 (s, 3H), 0.85 (m, 1H), 0.84 (s, 3H), 0.82 (s, 3H).

Example 10

0.05 g (0.6 mmol) of compound 3 prepared in example 3 was mixed with 0.011 g (0.7 mmol) of β-alanine ethyl ester hydrochloride and 2 mL of methanol, 0.05 g (8 mmol) of sodium cyanoborohydride was added under the conditions of ice bath and magnetic stirring at 1200 rpm, and a reductive amination reaction was carried out at room temperature for 1 hour; the material obtained after the reductive amination reaction was extracted with ethyl acetate for three times (the volume of ethyl acetate required for each time of extraction was 50 mL), then was washed with saturated sodium chloride solution for four times to obtain a clear solution (the volume of saturated sodium chloride solution required for each time of washing was 60 mL), the clear solution was distilled under reduced pressure to remove solvent, the obtained crude product was mixed with 5 mL of ethyl acetate, the mixture was used for a column chromatography after silica gel mixing. A mixture of ethyl acetate and n-hexane was used as an eluent (the volume ratio of Example 11

0.05 g (0.6 mmol) of compound 3 prepared in example 3 was mixed with 0.015 g (0.7 mmol) of diethyl aminomalonate hydrochloride and 2 mL of methanol, 0.05 g (8 mmol) of sodium cyanoborohydride was added under the conditions of ice bath and magnetic stirring at 1100 rpm, and a reductive amination reaction was carried out at room temperature for 1 hour; the material obtained after the reductive amination reaction was extracted with ethyl acetate for three times (the volume of ethyl acetate required for each time of extraction was 40 mL), then was washed with saturated sodium chloride solution for four times to obtain a clear solution (the volume of saturated sodium chloride solution required for each time of washing was 70 mL), the clear solution was distilled under reduced pressure to remove solvent, the obtained crude product was mixed with 4 mL of ethyl acetate, the mixture was used for a column chromatography after silica gel mixing. A mixture of ethyl acetate and n-hexane was used as an eluent (the volume ratio of ethyl acetate to n-hexane was 1:4), 0.03 g of target compound 11 was obtained as a white solid, yield: 50%. The structure of the target compound 11 is:

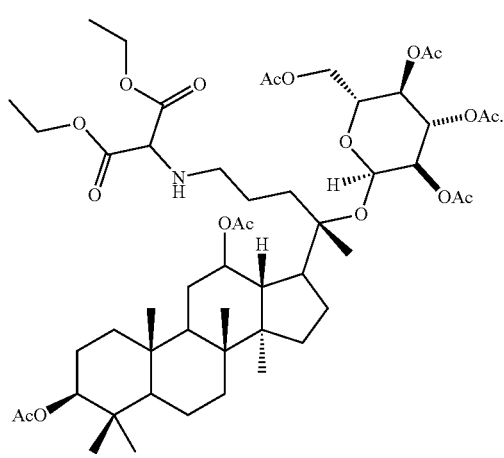

$^1$H NMR (600 MHz, cdcl$_3$) δ 5.16 (t, 1H), 4.97 (t, 1H), 4.89 (dd, 8.0 Hz, 1H), 4.78 (ddd, 1H), 4.66 (d, 1H), 4.46 (d, 1H), 4.11 (m, 5.3 Hz, 4H), 4.09 (m, 2H), 3.60 (ddd, 1H), 2.77 (ddd, 1H), 2.540 (m, 1H), 2.283 (m, 1H), 2.062 (m, 2H), 2.00 (m, 18H), 1.82 (dd, 1H), 1.81 (m, 1H), 1.74 (t, 1H), 1.67 (s, 3H), 1.65 (m, 3H), 1.63 (m, 3H), 1.53 (m, 2H), 1.55 (m, 2H), 1.49 (m, 2H), 1.39 (m, 2H), 1.37 (m, 1H), 1.33 (s, 3H), 1.25 (m, 2H), 1.220 (m, 1H), 1.07 (m, 2H), 1.01 (s, 3H), 0.96 (s, 3H), 0.92 (s, 3H), 0.91 (s, 3H), 0.77 (s, 3H).

Example 12

0.05 g (0.6 mmol) of compound 3 prepared in example 3 was mixed with 0.01 g (0.7 mmol) of L-phenylalanine methyl ester hydrochloride and 2 mL of methanol, 0.05 g (8 mmol) of sodium cyanoborohydride was added under the conditions of ice bath and magnetic stirring at 1100 rpm, and a reductive amination reaction was carried out at room temperature for 1 hour; the material obtained after the reductive amination reaction was extracted with ethyl acetate for three times (the volume of ethyl acetate required for each time of extraction was 30 mL), then was washed with saturated sodium chloride solution for four times to obtain a clear solution (the volume of saturated sodium chloride solution required for each time of washing was 80 mL), the clear solution was distilled under reduced pressure to remove solvent, the obtained crude product was mixed with 3 mL of ethyl acetate, the mixture was used for a column chromatography after silica gel mixing. A mixture of ethyl acetate and n-hexane was used as an eluent (the volume ratio of ethyl acetate to n-hexane was 1:3), 0.03 g of target compound 12 was obtained as a white solid, yield: 50%. The structure of the target compound 12 is:

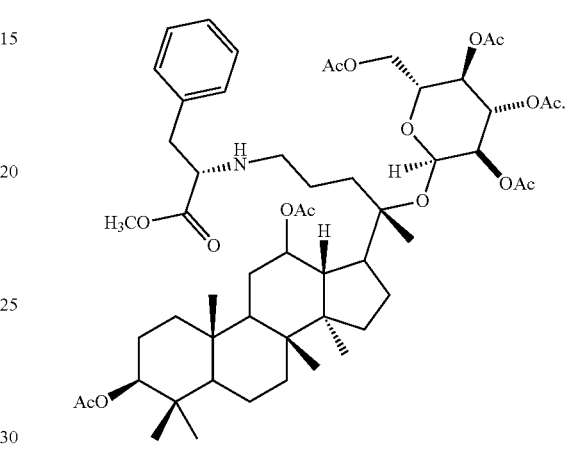

$^1$H NMR (600 MHz, cdcl$_3$) δ 7.31 (t, 1H), 7.11 (m, 5H), 5.32 (m, 1H), 4.96 (m, 1H), 4.79 (m, 2H), 4.61 (t, 1H), 4.42 (m, 1H), 4.31 (m, 1H), 4.16 (dd, 1H), 4.06 (t, 1H), 3.70 (s, 3H), 3.32 (m, 1H), 2.94 (m, 2H), 2.55 (m, 2H), 2.283 (m, 1H), 2.062 (m, 2H), 2.00 (ddd, 18H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.94 (s, 3H), 0.92 (s, 3H), 0.85 (m, 1H), 0.84 (s, 3H), 0.82 (s, 3H).

Example 13

0.05 g (0.6 mmol) of compound 3 prepared in example 3 was mixed with 0.014 g (0.7 mmol) of L-tyrosine methyl ester and 2 mL of methanol, 0.05 g (8 mmol) of sodium cyanoborohydride was added under the conditions of ice bath and magnetic stirring at 1100 rpm, and a reductive amination reaction was carried out at room temperature for 1 hour; the material obtained after the reductive amination reaction was extracted with ethyl acetate for three times (the volume of ethyl acetate required for each time of extraction was 20 mL), then was washed with saturated sodium chloride solution for four times to obtain a clear solution (the volume of saturated sodium chloride solution required for each time of washing was 90 mL), the clear solution was distilled under reduced pressure to remove solvent, the obtained crude product was mixed with 2 mL of ethyl acetate, the mixture was used for a column chromatography after silica gel mixing. A mixture of ethyl acetate and n-hexane was used as an eluent (the volume ratio of ethyl acetate to n-hexane was 1:2), 0.02 g of target compound 13 was obtained as a white solid, yield: 35%. The structure of the target compound 13 is:

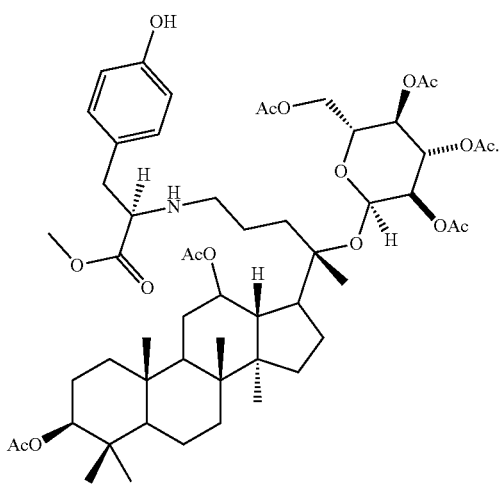

¹H NMR (600 MHz, cdcl₃) δ 7.01 (d, 2H), 6.75 (d, 2H), 6.04 (m, 1H), 5.49 (dd, 1H), 5.18 (m, 2H), 4.56 (m, 1H), 4.50 (s, 2H), 4.37 (m, 1H), 4.28 (m, 1H), 4.18 (m, 1H), 3.63 (m, 3H), 3.25 (s, 1H), 2.97 (m, 1H), 2.57 (t, 2H), 2.28 (m, 1H), 2.06 (m, 2H), 2.00 (ddd, 18H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.94 (s, 3H), 0.92 (s, 3H), 0.85 (m, 1H), 0.84 (s, 3H), 0.82 (s, 3H).

Example 14

0.05 g (0.6 mmol) of compound 3 prepared in example 3 was mixed with 0.017 g (0.7 mmol) of L-histidine methyl ester hydrochloride and 2 mL of methanol, 0.05 g (8 mmol) of sodium cyanoborohydride was added under the conditions of ice bath and magnetic stirring at 900 rpm, and a reductive amination reaction was carried out at room temperature for 1 hour; the material obtained after the reductive amination reaction was extracted with ethyl acetate for three times (the volume of ethyl acetate required for each time of extraction was 10 mL), then was washed with saturated sodium chloride solution for four times to obtain a clear solution (the volume of saturated sodium chloride solution required for each time of washing was 100 mL), the clear solution was distilled under reduced pressure to remove solvent, the obtained crude product was mixed with 1 mL of ethyl acetate, the mixture was used for a column chromatography after silica gel mixing. A mixture of ethyl acetate and n-hexane was used as an eluent (the volume ratio of ethyl acetate to n-hexane was 1:1), 0.03 g of target compound 14 was obtained as a white solid, yield: 51%. The structure of the target compound 14 is:

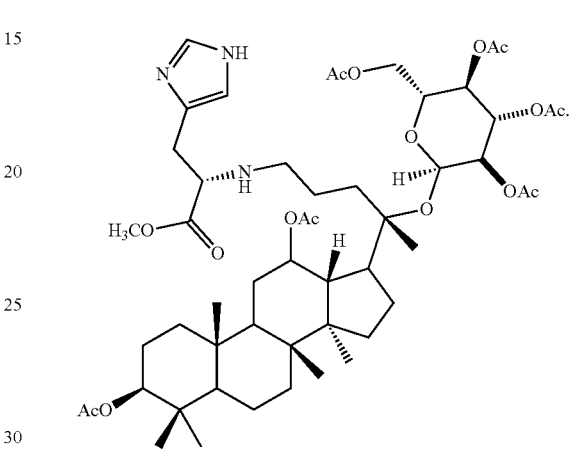

¹H NMR (600 MHz, cdcl₃) δ 8.67 (d, 1H), 7.63 (d, 1H), 6.02 (t, 1H), 5.90 (dd, 1H), 4.99 (m, 1H), 4.75 (t, 1H), 4.55 (m, 1H), 4.42 (m, 2H), 4.26 (m, 1H), 4.16 (m, 1H), 3.66 (s, 3H), 3.48 (t, 1H), 3.14 (m, 1H), 2.77 (m, 1H), 2.55 (m, 2H), 2.283 (m, 1H), 2.062 (m, 2H), 2.00 (ddd, 18H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.94 (s, 3H), 0.92 (s, 3H), 0.85 (m, 1H), 0.84 (s, 3H), 0.82 (s, 3H).

Example 15

0.05 g (0.6 mmol) of compound 3 prepared in example 3 was mixed with 0.015 g (0.7 mmol) of L-tryptophan methyl ester hydrochloride and 2 mL of methanol, 0.05 g (8 mmol) of sodium cyanoborohydride was added under the conditions of ice bath and magnetic stirring at 800 rpm, and a reductive amination reaction was carried out at room temperature for 1 hour; the material obtained after the reductive amination reaction was extracted with ethyl acetate for three times (the volume of ethyl acetate required for each time of extraction was 50 mL), then was washed with saturated sodium chloride solution for four times to obtain a clear solution (the volume of saturated sodium chloride solution required for each time of washing was 50 mL), the clear solution was distilled under reduced pressure to remove solvent, the obtained crude product was mixed with 5 mL of ethyl acetate, the mixture was used for a column chromatography after silica gel mixing. A mixture of ethyl acetate and n-hexane was used as an eluent (the volume ratio of ethyl acetate to n-hexane was 1:5), 0.02 g of target compound 15 was obtained as a white solid, yield: 33%. The structure of the target compound 15 is:

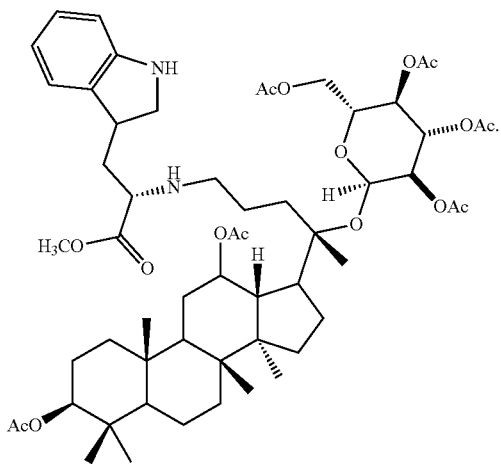

¹H NMR (600 MHz, cdcl₃) δ 7.26 (dd, 1H), 6.85 (ddd, 1H), 6.76 (ddd, 1H), 6.67 (ddd, 1H), 6.26 (t, 1H), 5.15 (t, 1H), 4.92 (m, 1H), 4.55 (dd, 1H), 4.44 (m, 1H), 4.28 (t, 1H), 4.11 (m, 2H), 3.68 (s, 3H), 3.52 (m, 2H), 3.45 (m, 1H), 3.37 (m, 1H), 2.54 (m, 2H), 2.48 (m, 1H), 2.20 (m, 1H), 2.283 (m, 1H), 2.062 (m, 2H), 2.00 (ddd, 18H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.94 (s, 3H), 0.92 (s, 3H), 0.85 (m, 1H), 0.84 (s, 3H), 0.82 (s, 3H).

Example 16

1 g (21 mmol) of a compound having a structure shown in formula V was mixed with 10 mL of acetic anhydride and 10 mL of pyridine, and a nucleophilic substitution reaction was carried out under the conditions of magnetic stirring at 1000 rpm and 60° C. for 3 hours; the material obtained after the nucleophilic substitution reaction was distilled under reduced pressure, the obtained crude product was mixed with 5 mL of ethyl acetate, and the mixture was used for a column chromatography after silica gel mixing. A mixture of ethyl acetate and n-hexane was used as an eluent (the volume ratio of ethyl acetate to n-hexane was 1:5), 1.1 g of compound 16 was obtained as a white solid, yield: 90%. The structure of the compound 16 is:

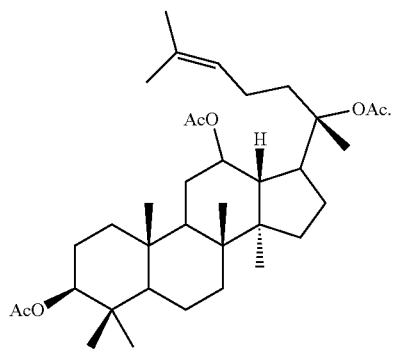

Example 17

1 g (17 mmol) of the compound 16 prepared in example 16, 5 mL of dichloromethane and 0.31 g (11 mmol) of meta-chloroperbenzoic acid were mixed, and a primary oxidation reaction was carried out at room temperature for 1 hour; 40 mL of water was added to the material obtained after the primary oxidation reaction, magnetic stirring was carried out at 1000 rpm for 2 hours, a white solid was precipitated and filtered to obtain a clear solution, the clear solution was distilled under reduced pressure to remove solvent, the obtained crude product was mixed with 5 mL of ethyl acetate, and the mixture was used for a column chromatography after silica gel mixing. A mixture of ethyl acetate and n-hexane was used as an eluent (the volume ratio of ethyl acetate to n-hexane was 1:5), 0.92 g of compound 17 was obtained as a white solid, yield: 90%. The structure of the compound 17 is:

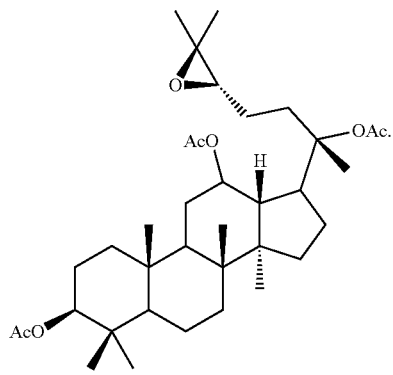

Example 18

0.9 g (15 mmol) of the compound 17 prepared in example 17, 5 mL of tetrahydrofuran and 0.83 g (32 mmol) of periodic acid were mixed, and a secondary oxidation reaction was carried out at room temperature for 2 hours; the material obtained after the secondary oxidation reaction was extracted with ethyl acetate for 3 times (the volume of ethyl acetate required for each time of extraction was 40 mL), then was washed with saturated sodium bicarbonate solution and saturated sodium chloride solution successively, four times for each solution to obtain a clear solution (the volume of saturated sodium bicarbonate solution required for each time of washing was 50 mL, the volume of saturated sodium chloride solution required for each time of washing was 50 mL), the clear solution was distilled under reduced pressure to remove solvent, the obtained crude product was mixed with 5 mL of ethyl acetate, the mixture was used for a column chromatography after silica gel mixing. A mixture of ethyl acetate and n-hexane was used as an eluent (the volume ratio of ethyl acetate to n-hexane was 1:5), 0.71 g of compound 18 was obtained as a white solid, yield: 85%. The structure of the compound 18 is:

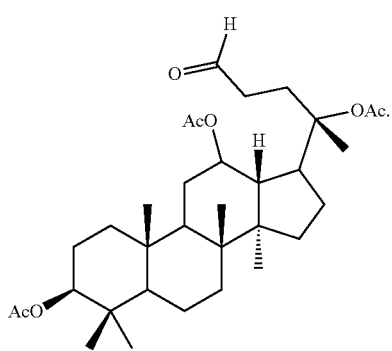

acetate and n-hexane was used as an eluent (the volume ratio of ethyl acetate to n-hexane was 1:10), 0.03 g of target compound 19 was obtained as a white solid, yield: 72%. The structure of the target compound 19 is:

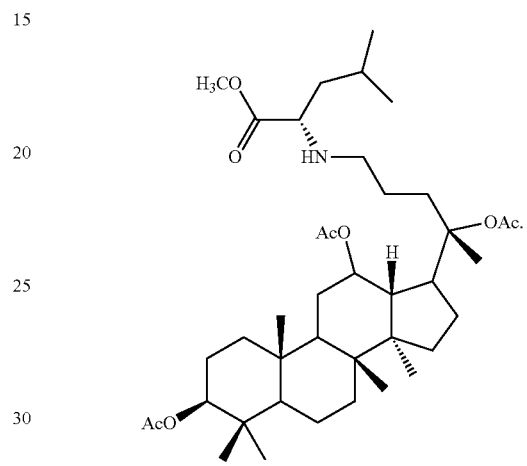

$^1$H NMR (600 MHz, cdcl$_3$) δ 4.95 (m, 1H), 4.25 (t, 1H), 3.65 (s, 3H), 2.88 (m, 1H), 2.56 (t, 2H), 2.00 (ddd, 9H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.94 (s, 3H), 0.92 (s, 3H), 0.85 (m, 1H), 0.84 (s, 3H), 0.82 (s, 3H).

Example 19

0.033 g (0.6 mmol) of the compound 18 prepared in example 18 was mixed with 0.013 g (0.7 mmol) of L-leucine methyl ester hydrochloride and 2 mL of methanol, 0.033 g (5.3 mmol) of sodium cyanoborohydride was added under the conditions of ice bath and magnetic stirring at 800 rpm, and a reductive amination reaction was carried out at room temperature for 1 hour; the material obtained after the reductive amination reaction was extracted with ethyl acetate for 3 times (the volume of ethyl acetate required for each time of extraction was 10 mL), then was washed with saturated sodium chloride solution for four times to obtain a clear solution (the volume of saturated sodium chloride solution required for each time of washing was 100 mL), the clear solution was distilled under reduced pressure to remove solvent, the obtained crude product was mixed with 10 mL of ethyl acetate, the mixture was used for a column chromatography after silica gel mixing. A mixture of ethyl Example 20

0.033 g (0.6 mmol) of the compound 18 prepared in example 18 was mixed with 0.012 g (0.7 mmol) of L-valine methyl ester hydrochloride and 2 mL of ethyl acetate, 0.033 g (5.3 mmol) of sodium borohydride was added under the conditions of ice bath and magnetic stirring at 1000 rpm, and a reductive amination reaction was carried out at room temperature for 3 hours; the material obtained after the reductive amination reaction was extracted with ethyl acetate for 3 times (the volume of ethyl acetate required for each time of extraction was 20 mL), then was washed with saturated sodium chloride solution for four times to obtain a clear solution (the volume of saturated sodium chloride solution required for each time of washing was 90 mL), the clear solution was distilled under reduced pressure to remove solvent, the obtained crude product was mixed with 9 mL of ethyl acetate, the mixture was used for a column chromatography after silica gel mixing. A mixture of ethyl acetate and n-hexane was used as an eluent (the volume ratio of ethyl acetate to n-hexane was 1:9), 0.03 g of target compound 20 was obtained as a white solid, yield: 75%. The structure of the target compound 20 is:

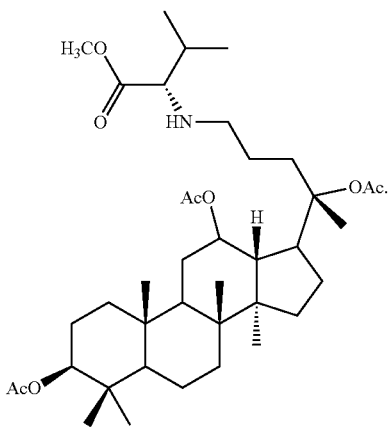

¹H NMR (600 MHz, cdcl₃) δ 4.95 (m, 1H), 4.25 (t, 1H), 3.65 (s, 3H), 2.88 (m, 1H), 2.56 (t, 2H), 2.00 (ddd, 9H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.98 (s, 3H), 0.94 (s, 3H), 0.96 (s, 3H), 0.92 (s, 3H), 0.85 (m, 1H), 0.84 (s, 3H), 0.82 (s, 3H).

Example 21

0.033 g (0.6 mmol) of the compound 18 prepared in example 18 was mixed with 0.012 g (0.7 mmol) of L-threonine methyl ester hydrochloride and 2 mL of chloroform, 0.033 g (5.3 mmol) of sodium triacetoxyborohydride was added under the conditions of ice bath and magnetic stirring at 1100 rpm, and a reductive amination reaction was carried out at room temperature for 6 hours; the material obtained after the reductive amination reaction was extracted with ethyl acetate for 3 times (the volume of ethyl acetate required for each time of extraction was 30 mL), then was washed with saturated sodium chloride solution for four times to obtain a clear solution (the volume of saturated sodium chloride solution required for each time of washing was 80 mL), the clear solution was distilled under reduced pressure to remove solvent, the obtained crude product was mixed with 8 mL of ethyl acetate, the mixture was used for a column chromatography after silica gel mixing. A mixture of ethyl acetate and n-hexane was used as an eluent (the volume ratio of ethyl acetate to n-hexane was 1:8), 0.04 g of target compound 21 was obtained as a white solid, yield: 50%. The structure of the target compound 21 is:

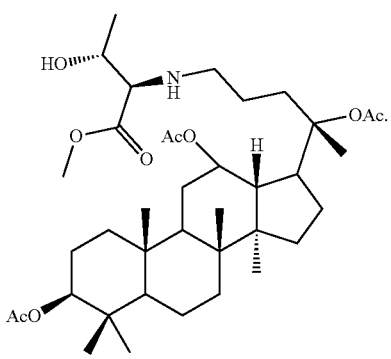

¹H NMR (600 MHz, cdcl₃) δ4.95 (m, 1H), 4.25 (t, 1H), 3.65 (s, 3H), 2.88 (m, 1H), 2.56 (t, 2H), 2.00 (ddd, 9H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.94 (s, 3H), 0.92 (s, 3H), 0.85 (m, 1H), 0.84 (s, 3H), 0.82 (s, 3H).

Example 22

0.033 g (0.6 mmol) of the compound 18 prepared in example 18 was mixed with 0.011 g (0.7 mmol) of L-serine methyl ester hydrochloride and 2 mL of dichloromethane, 0.033 g (5.3 mmol) of sodium cyanoborohydride was added under the conditions of ice bath and magnetic stirring at 1200 rpm, and a reductive amination reaction was carried out at room temperature for 9 hours; the material obtained after the reductive amination reaction was extracted with ethyl acetate for 3 times (the volume of ethyl acetate required for each time of extraction was 40 mL), then was washed with saturated sodium chloride solution for four times to obtain a clear solution (the volume of saturated sodium chloride solution required for each time of washing was 70 mL), the clear solution was distilled under reduced pressure to remove solvent, the obtained crude product was mixed with 7 mL of ethyl acetate, the mixture was used for a column chromatography after silica gel mixing. A mixture of ethyl acetate and n-hexane was used as an eluent (the volume ratio of ethyl acetate to n-hexane was 1:7), 0.028 g of target compound 22 was obtained as a white solid, yield: 73%. The structure of the target compound 22 is:

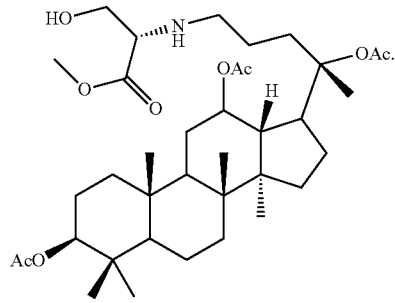

¹H NMR (600 MHz, cdcl₃) δ 4.95 (m, 1H), 4.25 (t, 1H), 3.65 (s, 3H), 2.88 (m, 1H), 2.56 (t, 2H), 2.00 (ddd, 9H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.94 (s, 3H), 0.92 (s, 3H), 0.85 (m, 1H), 0.84 (s, 3H), 0.82 (s, 3H)

Example 23

0.033 g (0.6 mmol) of the compound 18 prepared in example 18 was mixed with 0.017 g (0.7 mmol) of L-glutamic acid dimethyl ester hydrochloride and 2 mL of carbon tetrachloride, 0.033 g (5.3 mmol) of sodium cyanoborohydride was added under the conditions of ice bath and magnetic stirring at 1200 rpm, and a reductive amination reaction was carried out at room temperature for 1 hour; the material obtained after the reductive amination reaction was extracted with ethyl acetate for 3 times (the volume of ethyl acetate required for each time of extraction was 50 mL), then was washed with saturated sodium chloride solution for four times to obtain a clear solution (the volume of saturated sodium chloride solution required for each time of washing was 60 mL), the clear solution was distilled under reduced pressure to remove solvent, the obtained crude product was mixed with 6 mL of ethyl acetate, the mixture was used for a column chromatography after silica gel mixing. A mixture of ethyl acetate and n-hexane was used as an eluent (the volume ratio of ethyl acetate to n-hexane was 1:6), 0.028 g of target compound 23 was obtained as a white solid, yield: 67%. The structure of the target compound 23 is:

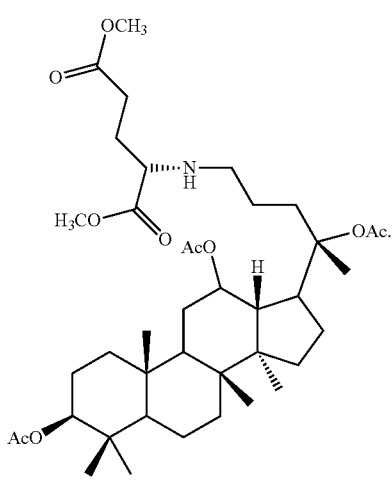

$^1$H NMR (600 MHz, cdcl$_3$) δ 4.95 (m, 1H), 4.25 (t, 1H), 3.65 (s, 3H), 2.88 (m, 1H), 2.56 (t, 2H), 2.00 (ddd, 9H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.94 (s, 3H), 0.92 (s, 3H), 0.85 (m, 1H), 0.84 (s, 3H), 0.82 (s, 3H).

Example 24

0.033 g (0.6 mmol) of the compound 18 prepared in example 18 was mixed with 0.009 g (0.7 mmol) of glycine methyl ester hydrochloride and 2 mL of methanol, 0.033 g (5.3 mmol) of sodium cyanoborohydride was added under the conditions of ice bath and magnetic stirring at 1100 rpm, and a reductive amination reaction was carried out at room temperature for 1 hour; the material obtained after the reductive amination reaction was extracted with ethyl acetate for 3 times (the volume of ethyl acetate required for each time of extraction was 60 mL), then was washed with saturated sodium chloride solution for four times to obtain a clear solution (the volume of saturated sodium chloride solution required for each time of washing was 50 mL), the clear solution was distilled under reduced pressure to remove solvent, the obtained crude product was mixed with 5 mL of ethyl acetate, the mixture was used for a column chromatography after silica gel mixing. A mixture of ethyl acetate and n-hexane was used as an eluent (the volume ratio of ethyl acetate to n-hexane was 1:5), 0.026 g of target compound 24 was obtained as a white solid, yield: 70%. The structure of the target compound 24 is:

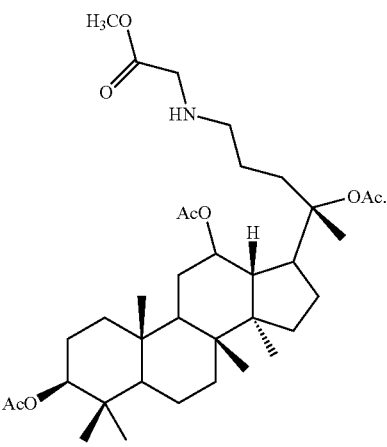

$^1$H NMR (600 MHz, cdcl$_3$) δ 4.95 (m, 1H), 4.25 (t, 1H), 3.65 (s, 3H), 2.88 (m, 1H), 2.56 (t, 2H), 2.00 (ddd, 9H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.94 (s, 3H), 0.92 (s, 3H), 0.85 (m, 1H), 0.84 (s, 3H), 0.82 (s, 3H).

Example 25

0.033 g (0.6 mmol) of the compound 18 prepared in example 18 was mixed with 0.011 g (0.7 mmol) of β-alanine ethyl ester hydrochloride and 2 mL of methanol, 0.033 g (5.3 mmol) of sodium cyanoborohydride was added under the conditions of ice bath and magnetic stirring at 1000 rpm, and a reductive amination reaction was carried out at room temperature for 1 hour; the material obtained after the reductive amination reaction was extracted with ethyl acetate for 3 times (the volume of ethyl acetate required for each time of extraction was 70 mL), then was washed with saturated sodium chloride solution for four times to obtain a clear solution (the volume of saturated sodium chloride solution required for each time of washing was 40 mL), the clear solution was distilled under reduced pressure to remove solvent, the obtained crude product was mixed with 4 mL of ethyl acetate, the mixture was used for a column chromatography after silica gel mixing. A mixture of ethyl acetate and n-hexane was used as an eluent (the volume ratio of ethyl acetate to n-hexane was 1:4), 0.025 g of target compound 25 was obtained as a white solid, yield: 65%. The structure of the target compound 25 is:

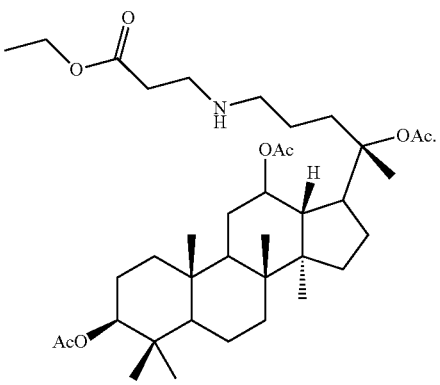

¹H NMR (600 MHz, cdcl₃) δ 4.95 (m, 1H), 4.25 (t, 1H), 3.92 (t, 2H), 2.93 (t, 2H), 2.56 (t, 2H), 2.46 (t, 2H), 2.00 (ddd, 9H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.94 (s, 3H), 0.92 (s, 3H), 0.85 (m, 1H), 0.84 (s, 3H), 0.82 (s, 3H).

Example 26

0.033 g (0.6 mmol) of the compound 18 prepared in example 18 was mixed with 0.015 g (0.7 mmol) of diethyl aminomalonate hydrochloride and 2 mL of methanol, 0.033 g (5.3 mmol) of sodium cyanoborohydride was added under the conditions of ice bath and magnetic stirring at 900 rpm, and a reductive amination reaction was carried out at room temperature for 1 hour; the material obtained after the reductive amination reaction was extracted with ethyl acetate for 3 times (the volume of ethyl acetate required for each time of extraction was 80 mL), then was washed with saturated sodium chloride solution for four times to obtain a clear solution (the volume of saturated sodium chloride solution required for each time of washing was 30 mL), the clear solution was distilled under reduced pressure to remove solvent, the obtained crude product was mixed with 3 mL of ethyl acetate, the mixture was used for a column chromatography after silica gel mixing. A mixture of ethyl acetate and n-hexane was used as an eluent (the volume ratio of ethyl acetate to n-hexane was 1:3), 0.026 g of target compound 26 was obtained as a white solid, yield: 60%. The structure of the target compound 26 is:

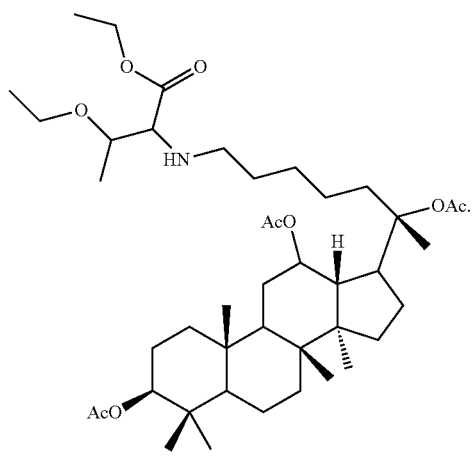

¹H NMR (600 MHz, cdcl₃) δ 4.95 (m, 1H), 4.25 (t, 1H), 2.88 (m, 1H), 2.56 (t, 2H), 2.00 (ddd, 9H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.07 (m, 3H), 1.03 (m, 1H), 0.94 (s, 3H), 0.92 (s, 3H), 0.85 (m, 1H), 0.84 (s, 3H), 0.82 (s, 3H).

Example 27

0.033 g (0.6 mmol) of the compound 18 prepared in example 18 was mixed with 0.01 g (0.7 mmol) of L-phenylalanine methyl ester hydrochloride and 2 mL of methanol, 0.033 g (5.3 mmol) of sodium cyanoborohydride was added under the conditions of ice bath and magnetic stirring at 800 rpm, and a reductive amination reaction was carried out at room temperature for 1 hour; the material obtained after the reductive amination reaction was extracted with ethyl acetate for 3 times (the volume of ethyl acetate required for each time of extraction was 90 mL), then was washed with saturated sodium chloride solution for four times to obtain a clear solution (the volume of saturated sodium chloride solution required for each time of washing was 20 mL), the clear solution was distilled under reduced pressure to remove solvent, the obtained crude product was mixed with 2 mL of ethyl acetate, the mixture was used for a column chromatography after silica gel mixing. A mixture of ethyl acetate and n-hexane was used as an eluent (the volume ratio of ethyl acetate to n-hexane was 1:2), 0.029 g of target compound 27 was obtained as a white solid, yield: 70%. The structure of the target compound 27 is:

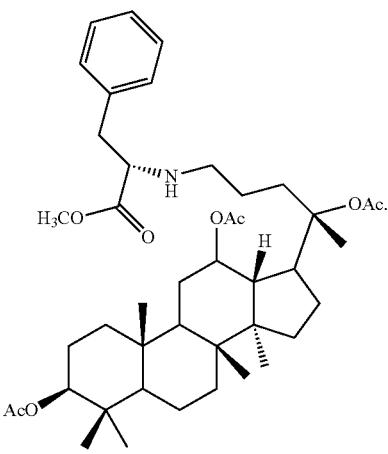

¹H NMR (600 MHz, cdcl₃) δ 7.31 (t, 1H), 7.11 (m, 5H), 64.95 (m, 1H), 4.25 (t, 1H), 2.88 (m, 1H), 2.56 (t, 2H), 2.00 (ddd, 9H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.94 (s, 3H), 0.92 (s, 3H), 0.85 (m, 1H), 0.84 (s, 3H), 0.82 (s, 3H).

Example 28

0.033 g (0.6 mmol) of the compound 18 prepared in example 18 was mixed with 0.014 g (0.7 mmol) of L-tyrosine methyl ester and 2 mL of methanol, 0.033 g (5.3 mmol) of sodium cyanoborohydride was added under the conditions of ice bath and magnetic stirring at 1000 rpm, and a reductive amination reaction was carried out at room temperature for 1 hour; the material obtained after the reductive amination reaction was extracted with ethyl acetate for 3 times (the volume of ethyl acetate required for each time of extraction was 100 mL), then was washed with saturated sodium chloride solution for four times to obtain a clear solution (the volume of saturated sodium chloride solution required for each time of washing was 10 mL), the clear solution was distilled under reduced pressure to remove solvent, the obtained crude product was mixed with 1 mL of ethyl acetate, the mixture was used for a column chromatography after silica gel mixing. A mixture of ethyl acetate and n-hexane was used as an eluent (the volume ratio of ethyl acetate to n-hexane was 1:1), 0.024 g of target compound 28 was obtained as a white solid, yield: 55%. The structure of the target compound 28 is:

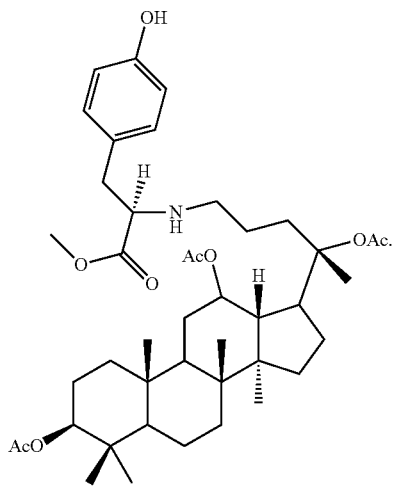

¹H NMR (600 MHz, cdcl₃) δ 7.01 (d, 2H), 6.75 (d, 2H), 64.95 (m, 1H), 4.25 (t, 1H), 3.66 (s, 3H), 3.50 (t, 1H), 3.25 (m, 1H), 3.05 (m, 1H), 2.56 (t, 2H), 2.00 (ddd, 9H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.94 (s, 3H), 0.92 (s, 3H), 0.85 (m, 1H), 0.84 (s, 3H), 0.82 (s, 3H).

Example 29

0.033 g (0.6 mmol) of the compound 18 prepared in example 18 was mixed with 0.017 g (0.7 mmol) of L-histidine methyl ester hydrochloride and 2 mL of methanol, 0.033 g (5.3 mmol) of sodium cyanoborohydride was added under the conditions of ice bath and magnetic stirring at 1000 rpm, and a reductive amination reaction was carried out at room temperature for 1 hour; the material obtained after the reductive amination reaction was extracted with ethyl acetate for 3 times (the volume of ethyl acetate required for each time of extraction was 50 mL), then was washed with saturated sodium chloride solution for four times to obtain a clear solution (the volume of saturated sodium chloride solution required for each time of washing was 50 mL), the clear solution was distilled under reduced pressure to remove solvent, the obtained crude product was mixed with 5 mL of ethyl acetate, the mixture was used for a column chromatography after silica gel mixing. A mixture of ethyl acetate and n-hexane was used as an eluent (the volume ratio of ethyl acetate to n-hexane was 1:5), 0.025 g of target compound 29 was obtained as a white solid, yield: 50%. The structure of the target compound 29 is:

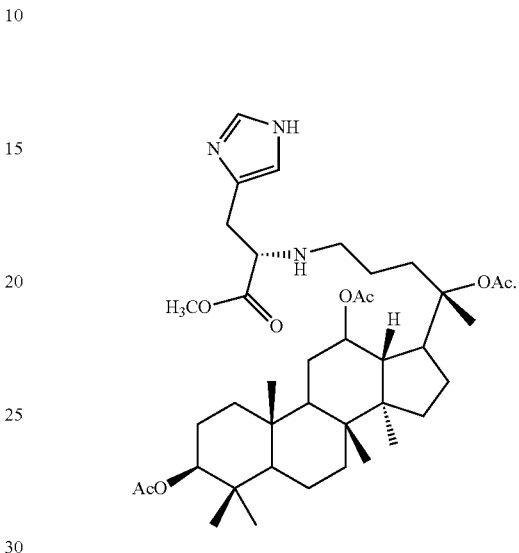

¹H NMR (600 MHz, cdcl₃) δ 8.73 (d, 1H), 7.65 (d, 1H), 4.95 (m, 1H), 4.25 (t, 1H), 3.45 (t, 2H), 3.98 (dd, 1H), 2.82 (dd, 1H), 2.56 (t, 2H), 2.00 (ddd, 9H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.94 (s, 3H), 0.92 (s, 3H), 0.85 (m, 1H), 0.84 (s, 3H), 0.82 (s, 3H).

Example 30

0.033 g (0.6 mmol) of the compound 18 prepared in example 18 was mixed with 0.015 g (0.7 mmol) of L-tryptophan methyl ester hydrochloride and 2 mL of methanol, 0.033 g (5.3 mmol) of sodium cyanoborohydride was added under the conditions of ice bath and magnetic stirring at 1000 rpm, and a reductive amination reaction was carried out at room temperature for 1 hour; the material obtained after the reductive amination reaction was extracted with ethyl acetate for 3 times (the volume of ethyl acetate required for each time of extraction was 50 mL), then was washed with saturated sodium chloride solution for four times to obtain a clear solution (the volume of saturated sodium chloride solution required for each time of washing was 50 mL), the clear solution was distilled under reduced pressure to remove solvent, the obtained crude product was mixed with 5 mL of ethyl acetate, the mixture was used for a column chromatography after silica gel mixing. A mixture of ethyl acetate and n-hexane was used as an eluent (the volume ratio of ethyl acetate to n-hexane was 1:5), 0.02 g of target compound 30 was obtained as a white solid, yield: 45%. The structure of the target compound 30 is:

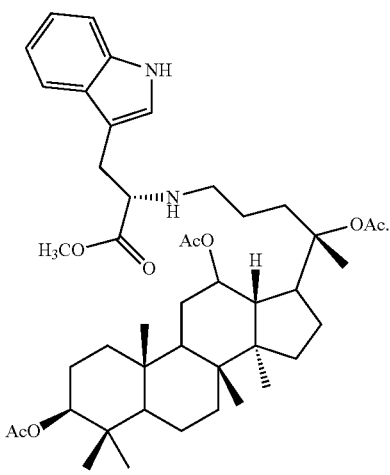

¹H NMR (600 MHz, cdcl₃) δ 7.26 (dd, 1H), 6.85 (ddd, 1H), 6.76 (ddd, 1H), 6.67 (ddd, 1H), 64.95 (t, 1H), 4.25 (m, 1H), 2.88 (m, 1H), 2.56 (t, 2H), 2.00 (ddd, 9H), 1.92 (m, 2H), 1.85 (m, 2H), 1.82 (m, 1H), 1.81 (m, 1H), 1.74 (m, 1H), 1.67 (m, 3H), 1.65 (m, 3H), 1.63 (m, 3H), 1.53 (m, 2H), 1.49 (m, 2H), 1.39 (m, 1H), 1.33 (m, 3H), 1.26 (m, 1H), 1.21 (m, 1H), 1.20 (m, 2H), 1.11 (s, 3H), 1.09 (m, 1H), 1.03 (m, 1H), 0.94 (s, 3H), 0.92 (s, 3H), 0.85 (m, 1H), 0.84 (s, 3H), 0.82 (s, 3H).

Example 31

The toxicities of the compounds prepared in Examples 1-30 of the present invention were tested, and the specific steps were as follows:

186 Kunming mice (18-22 g, males, purchased from the Experimental Animal Center of the Third Military Medical University) were randomly and averagely divided into 31 groups, and the compounds prepared in Examples 1-30 of the present invention were applied to the Kunming mice (intragastric administered 500 mg/kg at one time), and a saline control group (1 mL) was provided, the mice were observed continuously for 14 days.

Results: the Kunming mice in each experimental group were not dead and were in good condition, had normal food intake and hair color, and there was no significant difference between the body weight of the mice in the experimental groups and that of the saline control group.

In order to further verify the toxicities of the compounds prepared in Examples 1-30 of the present invention, the mouse macrophage cell line RAW264.7 was cultured, and the compounds prepared in Examples 1-30 of the invention were prepared to a concentration of 10 prnol/L using culture medium, wherein the solvent was normal saline, the co-solvent was dimethyl sulfoxide (DMSO, the final concentratoin was 0.1%), and a 0.1% DMSO saline control group was provided. The cell survival rate was determined by CCK8 method. The data were expressed as x̄±s. SPSS 10.0 line single-factor analysis of variance was performed among groups. The difference was significant when p<0.05. The results are shown in Table 1. As can be seen from Table 1, Compounds 1, 2 and 3 have significant cytotoxicities, and other compounds have no significant cytotoxicities at this concentration.

TABLE 1

Effects of the compounds prepared in Examples 1-30 on the survival rates of RAW264.7 cells ($\bar{x} \pm s$, n = 3)

| Group | Cell Survival Rate |
| --- | --- |
| Normal Saline Control Group | 1 |
| Dimethyl Sulfoxide ( DMSO ) Solvent Control Group | 0.95 ± 0.18 |
| Compound 1 | 0.65 ± 0.07 [a] |
| Compound 2 | 0.51 ± 0.08 [a] |
| Compound 3 | 0.42 ± 0.03 [a] |
| Compound 4 | 0.84 ± 0.02 |
| Compound 5 | 0.87 ± 0.08 |
| Compound 6 | 0.83 ± 0.09 |
| Compound 7 | 0.86 ± 0.01 |
| Compound 8 | 0.82 ± 0.06 |
| Compound 9 | 0.85 ± 0.07 |
| Compound 10 | 0.82 ± 0.13 |
| Compound 11 | 0.84 ± 0.12 |
| Compound 12 | 0.87 ± 0.16 |
| Compound 13 | 0.85 ± 0.12 |
| Compound 14 | 0.83 ± 0.06 |
| Compound 15 | 0.88 ± 0.04 |
| Compound 16 | 0.88 ± 0.01 |
| Compound 17 | 0.87 ± 0.07 |
| Compound 18 | 0.85 ± 0.08 |
| Compound 19 | 0.91 ± 0.07 |
| Compound 20 | 1.02 ± 0.13 |
| Compound 21 | 0.94 ± 0.17 |
| Compound 22 | 1.03 ± 0.15 |
| Compound 23 | 1.01 ± 0.09 |
| Compound 24 | 0.89 ± 0.14 |
| Compound 25 | 0.98 ± 0.07 |
| Compound 26 | 0.94 ± 0.05 |
| Compound 27 | 0.87 ± 0.04 |
| Compound 28 | 0.89 ± 0.04 |
| Compound 29 | 1.00 ± 0.16 |
| Compound 30 | 0.95 ± 0.09 |

Note:
[a] compared with the saline control group, p < 0.05

Example 32

The effects of the compounds prepared in Examples 1-30 of the present invention on the percentages of areas of atherosclerotic plaque formation to the area of the entire artery in apoE-/- mice with a high-fat diet and the levels of low-density lipoprotein cholesterol and the levels of high-density lipoprotein, the specific steps are as follows:

1. animals: 160 ten-week-old, healthy and clean-grade apoE-/- mice (purchased from Peking University Experimental Animal Center), males, weight: 22-25 g, were housed in separate cages in a sterile laminar feeding room and fed freely. The mice were fed by a high-fat diet (conventional feed+0.15% cholesterol+21% lard) for 25 weeks, the room temperature was kept at 24° C., relative humidity: 50%, illumination time 7:30-19:30.

2. Grouping, administration method:
after 10 weeks of feeding, the animals were divided into the following 32 groups (n=5) by weight in a balanced and random manner, and killed 15 weeks after administration.

Normal saline control group: normal saline, intragastric administration.

Positive control group: simvastatin 10 mg/(kg·d), intragastric administration.

The compound groups prepared in Examples 1-30 of the present invention (30 groups in total): each was intragastric administered 30 mg/(kg·d).

3. Test indexes and methods:
① Analysis of the area of atherosclerotic plaque and its percentage to total area: after the animals were killed, the aortas were separated, from the roots of the aortas to the terminal bifurcations of the abdominal aortas. After formalin fixation, the aortas were stained with Sudan IV, the red stained parts were the areas of atherosclerotic lesions. The percentage of the area of the lesion area to total area was calculated using Image Pro Plus 5.0 software.

② Determination of the levels of total cholesterol (TC), low-density cholesterol lipoprotein (LDL-C) and high-density lipoprotein cholesterol (HDL-C): using ROCHE 7060 automatic biochemical analyzer for the determination.

③ Determination of TNF-α level: Millipore liquid phase chip method was used for the determination (Mcytomag-70K-3, Mouse Cytokine/Chemokine Magnetic Bead Panel).

4. Statistical analysis method:

Data were expressed as x̄±s, and SPSS 10.0 line single-factor analysis of variance was performed among groups, a significant difference was indicated when $p<0.05$.

5. Results:

① As shown in Table 2, the compounds prepared in Examples 1-30 of the present invention all significantly reduced the percentages of atherosclerotic plaque areas in apoE-/- mice, which were statistically different from the control group.

TABLE 2

The effects of the compounds prepared in Examples 1 to 30 on the percentages of atherosclerotic plaque areas to total aortic area in apoE-/-mice (x̄ ± s, n = 5)

| Group | Plaque area/total aorta area ( % ) |
|---|---|
| Normal saline control group | 14.67 ± 3.58 |
| Simvastatin | 7.95 ± 2.03 [a] |
| Compound 1 | 10.65 ± 2.62 [a] |
| Compound 2 | 8.27 ± 2.54 [a] |
| Compound 3 | 9.74 ± 3.19 [a] |
| Compound 4 | 9.52 ± 4.21 [a] |
| Compound 5 | 10.29 ± 2.67 [a] |
| Compound 6 | 8.16 ± 2.83 [a] |
| Compound 7 | 11.02 ± 2.71 [a] |
| Compound 8 | 9.31 ± 3.58 [a] |
| Compound 9 | 10.55 ± 2.19 [a] |
| Compound 10 | 8.52 ± 3.25 [a] |
| Compound 11 | 9.68 ± 3.52 [a] |
| Compound 12 | 10.23 ± 3.54 [a] |
| Compound 13 | 9.44 ± 3.24 [a] |
| Compound 14 | 9.34 ± 3.01 [a] |
| Compound 15 | 10.22 ± 2.19 [a] |
| Compound 16 | 10.41 ± 2.09 [a] |
| Compound 17 | 8.53 ± 2.57 [a] |
| Compound 18 | 9.15 ± 2.85 [a] |
| Compound 19 | 8.34 ± 2.41 [a] |
| Compound 20 | 9.67 ± 2.98 [a] |
| Compound 21 | 8.28 ± 3.29 [a] |
| Compound 22 | 10.32 ± 2.74 [a] |
| Compound 23 | 8.64 ± 2.46 [a] |
| Compound 24 | 9.54 ± 2.65 [a] |
| Compound 25 | 8.33 ± 2.44 [a] |
| Compound 26 | 9.78 ± 3.17 [a] |
| Compound 27 | 10.65 ± 3.82 [a] |
| Compound 28 | 8.18 ± 2.89 [a] |
| Compound 29 | 9.67 ± 2.51 [a] |
| Compound 30 | 9.99 ± 3.68 [a] |

Note:
[a] compared with the control group, $p < 0.05$

② As shown in Table 3, the compounds prepared in Examples 1-30 of the present invention can all significantly increase HDL-C levels, and some compounds significantly decreased the levels of LDL-C in the serums of mice, which were statistically different from the control group.

TABLE 3

Effects of the compounds prepared in Examples 1-30 on blood lipids in apoE-/-mice (mmol/L, x̄ ± s, n = 5)

| Group | LDL-C | HDL-C |
|---|---|---|
| Normal saline control group | 7.33 ± 1.03 | 3.74 ± 0.62 |
| Simvastatin | 2.75 ± 1.89 [a] | 3.69 ± 0.72 [a] |
| Compound 1 | 6.39 ± 1.09 | 4.55 ± 0.86 [a] |
| Compound 2 | 5.56 ± 1.24 [a] | 5.47 ± 0.91 [a] |
| Compound 3 | 6.12 ± 1.28 | 4.97 ± 0.95 [a] |
| Compound 4 | 4.62 ± 1.58 [a] | 5.48 ± 0.61 [a] |
| Compound 5 | 5.58 ± 1.89 [a] | 5.21 ± 0.73 [a] |
| Compound 6 | 6.04 ± 1.07 | 5.51 ± 0.94 [a] |
| Compound 7 | 5.50 ± 1.82 [a] | 4.52 ± 0.46 [a] |
| Compound 8 | 4.34 ± 1.19 [a] | 5.63 ± 0.84 [a] |
| Compound 9 | 6.84 ± 0.85 | 4.41 ± 0.67 [a] |
| Compound 10 | 6.54 ± 1.06 | 4.50 ± 0.94 [a] |
| Compound 11 | 6.59 ± 1.56 | 4.93 ± 0.58 [a] |
| Compound 12 | 5.27 ± 1.74 [a] | 4.44 ± 0.83 [a] |
| Compound 13 | 5.07 ± 0.99 [a] | 5.29 ± 1.18 [a] |
| Compound 14 | 5.58 ± 1.11 [a] | 4.39 ± 0.59 [a] |
| Compound 15 | 6.54 ± 1.36 | 4.12 ± 0.82 [a] |
| Compound 16 | 5.18 ± 1.26 [a] | 4.12 ± 0.90 [a] |
| Compound 17 | 4.83 ± 1.51 [a] | 5.55 ± 0.56 [a] |
| Compound 18 | 6.15 ± 1.28 | 4.72 ± 0.91 [a] |
| Compound 19 | 4.62 ± 1.34 [a] | 5.13 ± 0.83 [a] |
| Compound 20 | 6.62 ± 0.89 | 4.72 ± 0.52 [a] |
| Compound 21 | 4.31 ± 1.84 [a] | 5.82 ± 0.95 [a] |
| Compound 22 | 6.31 ± 1.17 | 4.29 ± 0.84 [a] |
| Compound 23 | 4.28 ± 1.46 [a] | 5.39 ± 0.61 [a] |
| Compound 24 | 5.65 ± 1.04 [a] | 4.68 ± 0.67 [a] |
| Compound 25 | 4.82 ± 1.54 [a] | 5.14 ± 0.87 [a] |
| Compound 26 | 6.28 ± 0.84 | 4.45 ± 0.62 [a] |
| Compound 27 | 5.55 ± 1.06 [a] | 4.37 ± 0.56 [a] |
| Compound 28 | 4.59 ± 1.62 [a] | 5.55 ± 0.63 [a] |
| Compound 29 | 6.27 ± 1.59 | 4.10 ± 0.78 [a] |
| Compound 30 | 6.37 ± 0.75 | 4.42 ± 0.57 [a] |

Note:
[a] compared with the control group, $p < 0.05$

③ As shown in Table 4, the compounds prepared in Examples 1-30 of the present invention can significantly reduce the local TNF-α levels in the arteries of apoE-/- mice, which were statistically different from the control group, indicating that the compounds prepared in Examples 1-30 of the present invention had good anti-inflammatory effects.

TABLE 4

Effects of the compounds prepared in Examples 1-30 on the local TNF-α levels in the arteries of apoE-/- mice (x̄ ± s, n = 5)

| Group | TNF-α level ( ng/g ) |
|---|---|
| Normal saline control group | 25.58 ± 6.44 |
| Simvastatin | 14.84 ± 3.22 [a] |
| Compound 1 | 19.41 ± 3.81 [a] |
| Compound 2 | 13.24 ± 3.71 [a] |
| Compound 3 | 16.68 ± 4.98 [a] |
| Compound 4 | 11.04 ± 3.68 [a] |
| Compound 5 | 17.73 ± 4.87 [a] |
| Compound 6 | 11.35 ± 4.97 [a] |
| Compound 7 | 17.77 ± 4.63 [a] |
| Compound 8 | 12.67 ± 3.11 [a] |
| Compound 9 | 12.85 ± 4.17 [a] |
| Compound 10 | 11.66 ± 2.65 [a] |
| Compound 11 | 12.33 ± 5.81 [a] |
| Compound 12 | 18.27 ± 5.24 [a] |
| Compound 13 | 15.65 ± 6.74 [a] |
| Compound 14 | 16.92 ± 5.04 [a] |
| Compound 15 | 16.07 ± 3.67 [a] |
| Compound 16 | 15.94 ± 4.29 [a] |
| Compound 17 | 15.27 ± 4.65 [a] |
| Compound 18 | 16.65 ± 4.57 [a] |
| Compound 19 | 11.23 ± 3.69 [a] |
| Compound 20 | 15.98 ± 5.33 [a] |

TABLE 4-continued

Effects of the compounds prepared in Examples 1-30 on the local TNF-α levels in the arteries of apoE-/- mice ($\bar{x} \pm s$, n = 5)

| Group | TNF-α level ( ng/g ) |
|---|---|
| Compound 21 | 10.76 ± 3.54 [a] |
| Compound 22 | 18.14 ± 6.82 [a] |
| Compound 23 | 12.61 ± 374 [a] |
| Compound 24 | 15.47 ± 2.88 [a] |
| Compound 25 | 11.65 ± 5.45 [a] |
| Compound 26 | 16.02 ± 3.11 [a] |
| Compound 27 | 17.95 ± 2.15 [a] |
| Compound 28 | 11.84 ± 2.91 [a] |
| Compound 29 | 14.93 ± 3.67 [a] |
| Compound 30 | 16.11 ± 4.19 [a] |

Note:
[a] compared with the control group, p < 0.05

Example 33

The effects of the compounds prepared in Examples 1-30 of the present invention on the formation of RAW264.7 cell-derived foam cells, the specific steps are as follows:

1. Cell culture and foam cell model establishment:

RAW264.7 cells were cultured in DMEM culture medium with high glucose level (GIBCO) to a cell concentration of $1\times10^6$, planted in a 6-well plate, and 60 mg/L of ox-LDL (oxidized modified low-density lipoprotein, Peking Union Medical College) was added, foam cells were obtained after 48 hours of incubation.

2. Grouping and index detection:

The obtained foam cells were divided into 61 groups, 3 well plates were included in one group. After the treatment by adding the drugs (100 μL/well) for 48 hours, the medium was discarded, and after oil red 0 staining, the excess amount of oil red 0 was washed away. The cells were dissolved in isopropanol and the absorbance values were measured at 490 nm. The OD value of the model group was 100%, and the OD value of each group corrected by the number of cells was compared with the model group to obtain the ratio of intracellular lipid content. The larger the value, the more intracellular lipids, the higher the degree of formation of foam cells.

Normal saline control group: normal saline

Low dose groups of the compounds prepared in Examples 1-30 of the present invention:

10 μmol/L (solvents were normal saline).

High dose groups of compounds prepared in Examples 1-30 of the present invention: 30 μmol/L (solvents were normal saline).

3. Statistical analysis method:

Data were expressed as $\bar{x} \pm s$, and SPSS 10.0 line single-factor analysis of variance was performed amoung groups, a significant difference was indicated when p<0.05.

4. Results: the compounds prepared in Examples 1-30 of the present invention can all significantly reduce the degrees of formation of foam cells at a dose of 30 μmol/L, and some compounds can significantly reduce the degrees of formation of foam cells at a dose of 10 μmol/L.

TABLE 5

Effects of the compounds prepared in Examples 1-30 of the present invention on the degrees of formation of RAW264.7-derived foam cells (%, $\bar{x} \pm s$, n = 3)

| Group | Dose ( μmol/L ) | Foam cell formation ( % ) |
|---|---|---|
| Normal saline control group | | 100 |
| Compound 1 | 10 | 83 ± 12 |
| | 30 | 65 ± 18 [a] |
| Compound 2 | 10 | 70 ± 25 [a] |
| | 30 | 64 ± 19 |
| Compound 3 | 10 | 85 ± 20 |
| | 30 | 72 ± 13 [a] |
| Compound 4 | 10 | 74 ± 15 [a] |
| | 30 | 54 ± 12 [a] |
| Compound 5 | 10 | 77 ± 18 [a] |
| | 30 | 62 ± 13 [a] |
| Compound 6 | 10 | 73 ± 16 [a] |
| | 30 | 48 ± 14 [a] |
| Compound 7 | 10 | 83 ± 13 |
| | 30 | 71 ± 13 [a] |
| Compound 8 | 10 | 73 ± 16 [a] |
| | 30 | 51 ± 17 [a] |
| Compound 9 | 10 | 79 ± 23 |
| | 30 | 65 ± 17 [a] |
| Compound 10 | 10 | 69 ± 18 [a] |
| | 30 | 45 ± 21 [a] |
| Compound 11 | 10 | 72 ± 14 [a] |
| | 30 | 65 ± 15 [a] |
| Compound 12 | 10 | 84 ± 15 |
| | 30 | 68 ± 21 [a] |
| Compound 13 | 10 | 71 ± 14 [a] |
| | 30 | 47 ± 23 [a] |
| Compound 14 | 10 | 78 ± 18 [a] |
| | 30 | 66 ± 16 [a] |
| Compound 15 | 10 | 68 ± 12 [a] |
| | 30 | 56 ± 22 [a] |
| Compound 16 | 10 | 81 ± 12 |
| | 30 | 72 ± 21 [a] |
| Compound 17 | 10 | 70 ± 15 [a] |
| | 30 | 55 ± 21 [a] |
| Compound 18 | 10 | 84 ± 16 |
| | 30 | 76 ± 14 [a] |
| Compound 19 | 10 | 63 ± 18 [a] |
| | 30 | 43 ± 9 [a] |
| Compound 20 | 10 | 79 ± 15 [a] |
| | 30 | 63 ± 14 [a] |
| Compound 21 | 10 | 65 ± 15 [a] |
| | 30 | 47 ± 13 [a] |
| Compound 22 | 10 | 76 ± 10 [a] |
| | 30 | 65 ± 14 [a] |
| Compound 23 | 10 | 68 ± 18 [a] |
| | 30 | 47 ± 19 [a] |
| Compound 24 | 10 | 79 ± 18 [a] |
| | 30 | 66 ± 16 [a] |
| Compound 25 | 10 | 62 ± 18 [a] |
| | 30 | 44 ± 15 [a] |
| Compound 26 | 10 | 83 ± 21 |
| | 30 | 72 ± 18 [a] |
| Compound 27 | 10 | 76 ± 12 [a] |
| | 30 | 65 ± 18 [a] |
| Compound 28 | 10 | 63 ± 11 [a] |
| | 30 | 45 ± 16 [a] |
| Compound 29 | 10 | 85 ± 10 |
| | 30 | 72 ± 18 [a] |
| Compound 30 | 10 | 78 ± 12 [a] |
| | 30 | 64 ± 13 [a] |

Note:
[a] compared with the control group, p < 0.05

As can be seen from the above examples, the panaxdiol-type ginsenoside derivatives provided by the present invention have low cytotoxicities, can significantly reduce the percentages of the areas of atherosclerotic plaques in apoE-/- mice, can also effectively reduce the levels of low-density lipoprotein cholesterol and increase the levels of high-density lipoprotein cholesterol in serums of mice, and can significantly reduce the local TNF-α levels in the arteries of apoE−/− mice and have good anti-inflammatory effects; at a dose of 30 μM, the panaxdiol-type ginsenoside derivatives can significantly reduce the degrees of the formation of RAW264.7 cell-derived foam cells. These indicate that the panaxdiol-type ginsenoside derivatives provided by the present invention can be used as active ingredients for the preparation of medicaments for preventing and treating atherosclerosis.

The above examples are only preferred embodiments of the present invention, and it should be noted that those skilled in the art can also make several improvements and modifications without departing from the principles of the present invention, and these improvements and modifications should be considered within the scope of protection of the present invention.

The invention claimed is:

1. A panaxdiol-type ginsenoside derivative, having the structure shown in formula I or formula II:

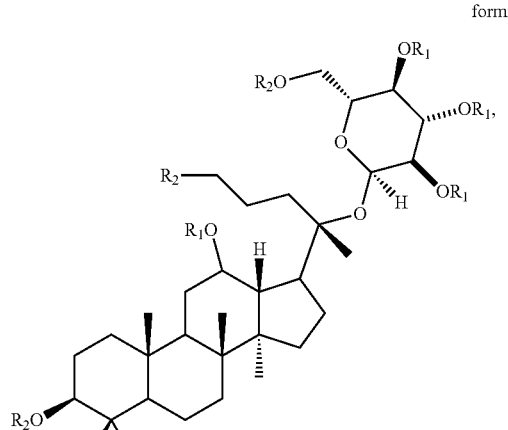

formula I

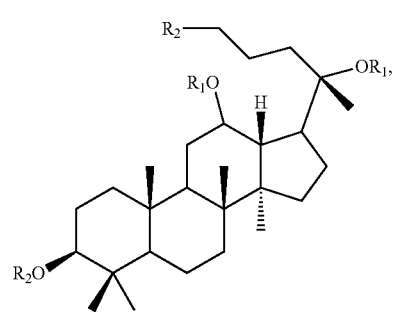

formula II in formula I and formula II, $R_1$ is

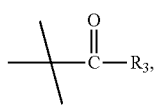

wherein, $R_3$ is a C1-C4 alkyl;

$R_2$ has the structure shown in formula III:

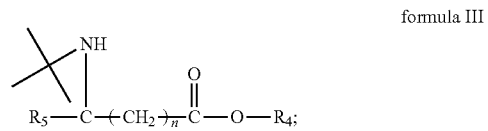

formula III in formula III, n=0, 1 or 2, $R_4$ is methyl or ethyl, $R_5$ is one of a hydrogen atom, a substituted or unsubstituted C1-C5 alkyl, a substituted or unsubstituted benzyl, a C4-C9 heterocycloalkyl or a C3-C5 ester alkyl;

or $R_2$ is

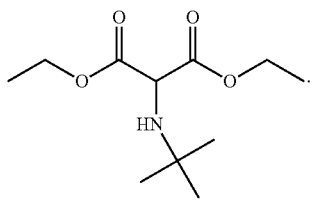 [SMILES: CCOC(=O)C(NC(C)(C)C)C(=O)OCC]

2. The panaxdiol-type ginsenoside derivative according to claim 1, wherein, $R_5$ is a C1-C5 alkyl, or a C1-C5 hydroxyalkyl.

3. The panaxdiol-type ginsenoside derivative according to claim 1, wherein, $R_5$ is —CH$_2$CH(CH$_3$)$_2$, —CH(CH$_3$)$_2$, —CH(OH)CH$_3$, —CH$_2$OH, —CH$_2$CH$_2$COOCH$_2$CH$_3$ or —CH$_2$COOCH$_2$CH$_3$.

4. The panaxdiol-type ginsenoside derivative according to claim 1, wherein, $R_5$ is

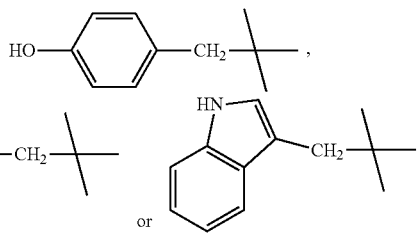

5. The panaxdiol-type ginsenoside derivative according to claim 1, wherein, $R_2$ is

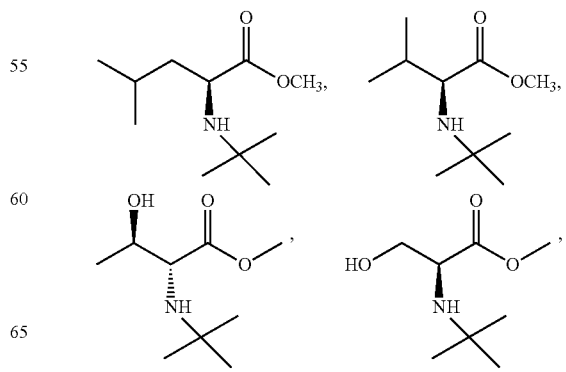

-continued

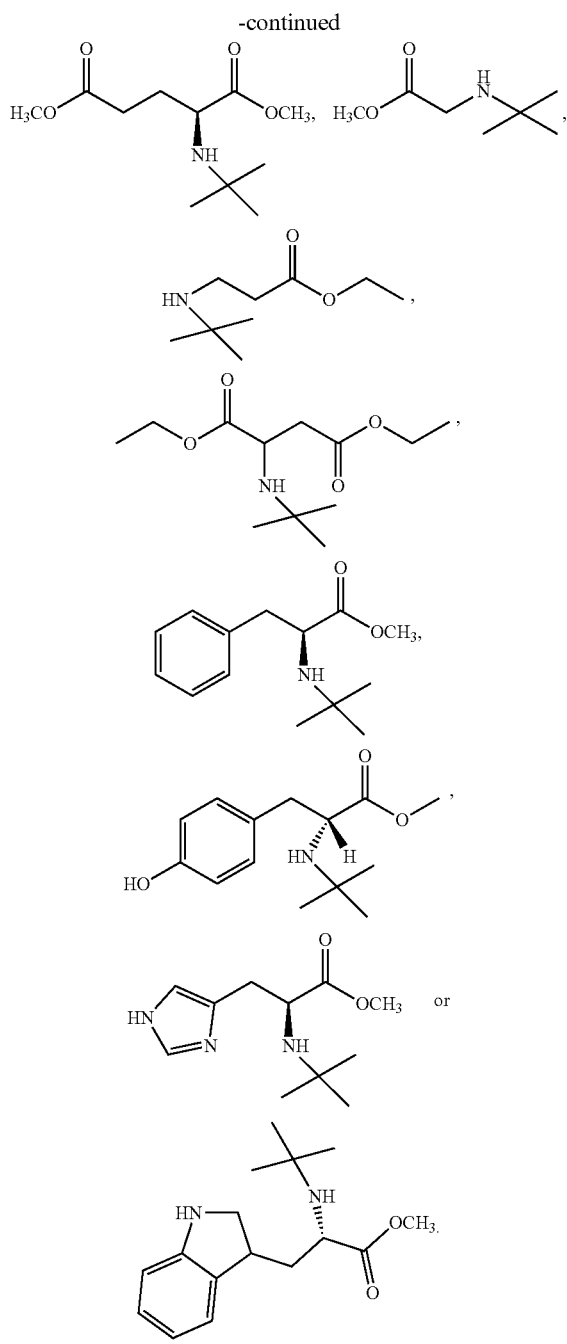

6. The panaxdiol-type ginsenoside derivative according to claim 1, wherein, $R_1$ is

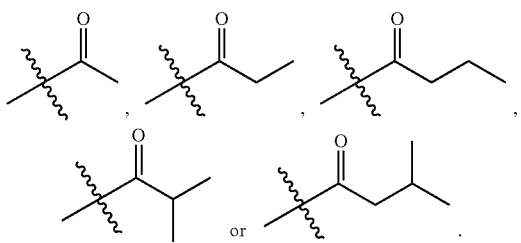

7. A preparation method of the panaxdiol-type ginsenoside derivative according to claim 1, comprising the following steps:
  (1) subjecting a parent compound to a nucleophilic substitution reaction with an acid anhydride in the presence of an alkaline reagent to obtain a first intermediate product;
  (2) subjecting the first intermediate product in step (1) to an oxidation reaction in the presence of an oxidizing agent and an organic solvent to obtain a second intermediate product;
  (3) subjecting the second intermediate product in step (2) to a reductive amination reaction with an amino compound in the presence of an organic solvent and a reducing agent to obtain the panaxdiol-type ginsenoside derivative having the structure shown in formula I or formula II;
wherein the parent compound in step (1) has the structure shown in formula IV or formula V:

formula IV

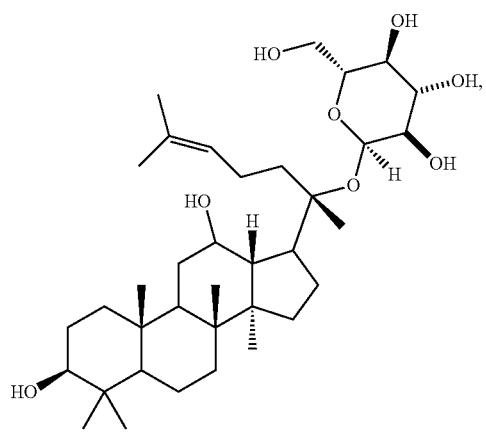

formula V

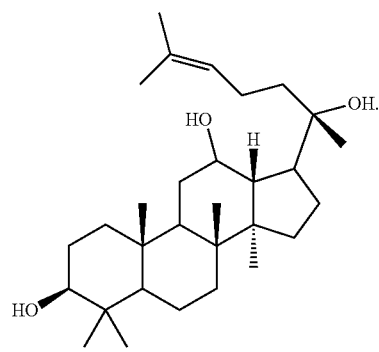

8. The preparation method according to claim 7, wherein, the oxidation reaction in step (2) is specifically:
  (21) subjecting the first intermediate product in step (1) to a primary oxidation reaction in the presence of a first oxidizing agent and an organic solvent to obtain a precursor of the second intermediate product;
  (22) subjecting the precursor of the second intermediate product in step (21) to a secondary oxidation reaction in the presence of a second oxidizing agent and an organic solvent to obtain the second intermediate product.

9. The preparation method according to claim 8, wherein, the first oxidizing agent in step (21) is hydrogen peroxide, hypochlorous acid, calcium hypochlorite, acetone peroxide or meta-chloroperbenzoic acid; the second oxidizing agent in step (22) is potassium permanganate, manganese dioxide, periodic acid or Sarrett reagent.

10. A method for preventing and treating atherosclerosis, comprising administering the panaxdiol-type ginsenoside derivative according to claim 1 to a subject.

* * * * *